US009808577B2

(12) United States Patent
Nagar et al.

(10) Patent No.: US 9,808,577 B2
(45) Date of Patent: Nov. 7, 2017

(54) DEVICE, SYSTEM AND METHOD FOR FACILITATING SYRINGE BASED DRUG DELIVERY AND MANAGEMENT THEREOF

(75) Inventors: Ron Nagar, Tel Aviv (IL); Gabriel Bitton, Jerusalem (IL); Elisha Amir, Livnim (IL); Moshe Fadlun, Rishon Lezion (IL)

(73) Assignee: Insuline Medical Ltd., Petach Tikva (IL)

( * ) Notice: Subject to any disclaimer, the term of this patent is extended or adjusted under 35 U.S.C. 154(b) by 1003 days.

(21) Appl. No.: 14/116,768

(22) PCT Filed: May 10, 2012

(86) PCT No.: PCT/IB2012/052335
§ 371 (c)(1),
(2), (4) Date: Mar. 31, 2014

(87) PCT Pub. No.: WO2012/153295
PCT Pub. Date: Nov. 15, 2012

(65) Prior Publication Data
US 2014/0207099 A1    Jul. 24, 2014

Related U.S. Application Data

(60) Provisional application No. 61/484,457, filed on May 10, 2011, provisional application No. 61/598,127, filed on Feb. 13, 2012.

(51) Int. Cl.
*A61K 9/22* (2006.01)
*A61M 5/172* (2006.01)
*A61M 5/142* (2006.01)
*A61M 5/50* (2006.01)

(52) U.S. Cl.
CPC ...... *A61M 5/1723* (2013.01); *A61M 5/14244* (2013.01); *A61M 5/14248* (2013.01); *A61M 5/50* (2013.01); *A61M 2205/3569* (2013.01); *A61M 2205/3576* (2013.01)

(58) Field of Classification Search
CPC ............ A61M 5/1413; A61M 5/14244; A61M 2205/3569; A61M 2205/3576; A61M 5/14248; A61M 5/1723; A61M 5/50; A61M 5/14; A61M 5/142; A61M 2005/14208;
(Continued)

(56) References Cited

FOREIGN PATENT DOCUMENTS

| IL | WO 2009125398 A2 * 10/2009 .......... A61M 5/1413 |
| WO | 2008114218 9/2008 |
| WO | 2008114220 9/2008 |

(Continued)

*Primary Examiner* — Jason Flick
(74) *Attorney, Agent, or Firm* — Daniel J. Swirsky; AlphaPatent Associates Ltd.

(57) ABSTRACT

The present invention relates to a device, system and a method for optimizing syringe based drug delivery profile with a treatment element and in particular, to such a device, system and method in which optimization is based on a plurality of data that directly and/or indirectly affect the optimization of the drug delivery profile. The device facilitating syringe based drug delivery, by optimizing drug delivery of the injected drug, records user's activity, and data relative to drug injections, comprising a disposable unit configured for a single use period and a rechargeable reusable unit having electronics comprising a sensor module.

21 Claims, 11 Drawing Sheets

(58) Field of Classification Search
CPC ......... A61M 2005/14252; A61M 2005/14268; A61M 5/168; A61M 5/172
USPC ..................................................... 604/890.1
See application file for complete search history.

(56) References Cited

FOREIGN PATENT DOCUMENTS

| | | |
|---|---|---|
| WO | 2008114223 | 9/2008 |
| WO | 2008114224 | 9/2008 |
| WO | 2009013735 | 1/2009 |
| WO | 2009016635 | 2/2009 |
| WO | 2009081262 | 7/2009 |
| WO | 2009125398 | 10/2009 |
| WO | 2009144726 | 12/2009 |
| WO | 2010041261 | 4/2010 |
| WO | 2010052579 | 5/2010 |
| WO | 2011016028 | 2/2011 |
| WO | 2011039736 | 4/2011 |
| WO | 2012164556 | 6/2012 |
| WO | 2012156967 | 11/2012 |
| WO | 2014064691 | 1/2014 |
| WO | 2014087242 | 12/2014 |
| WO | 2014136105 | 12/2014 |
| WO | 2015008169 | 1/2015 |
| WO | 2016071912 | 5/2016 |

* cited by examiner

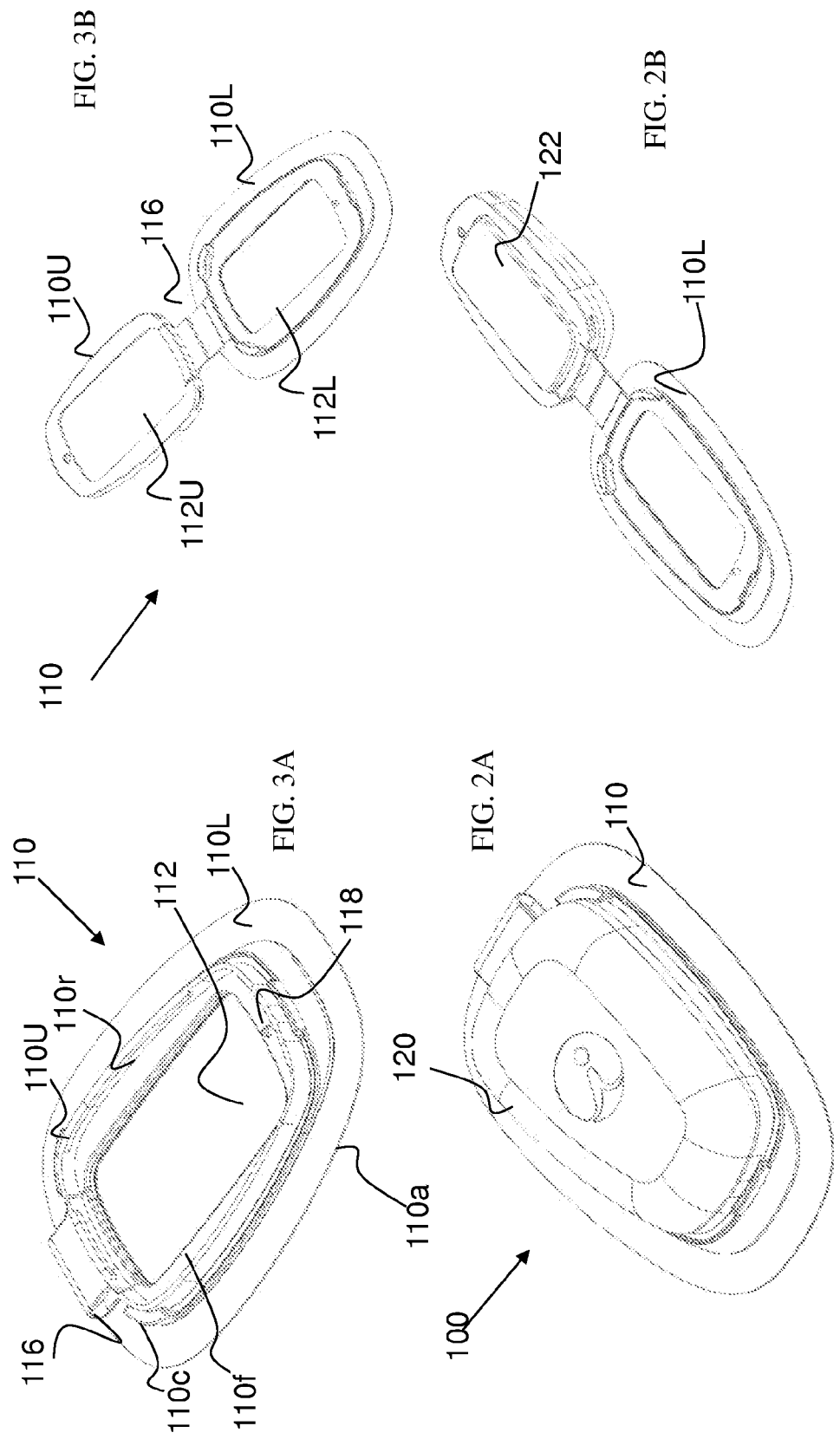

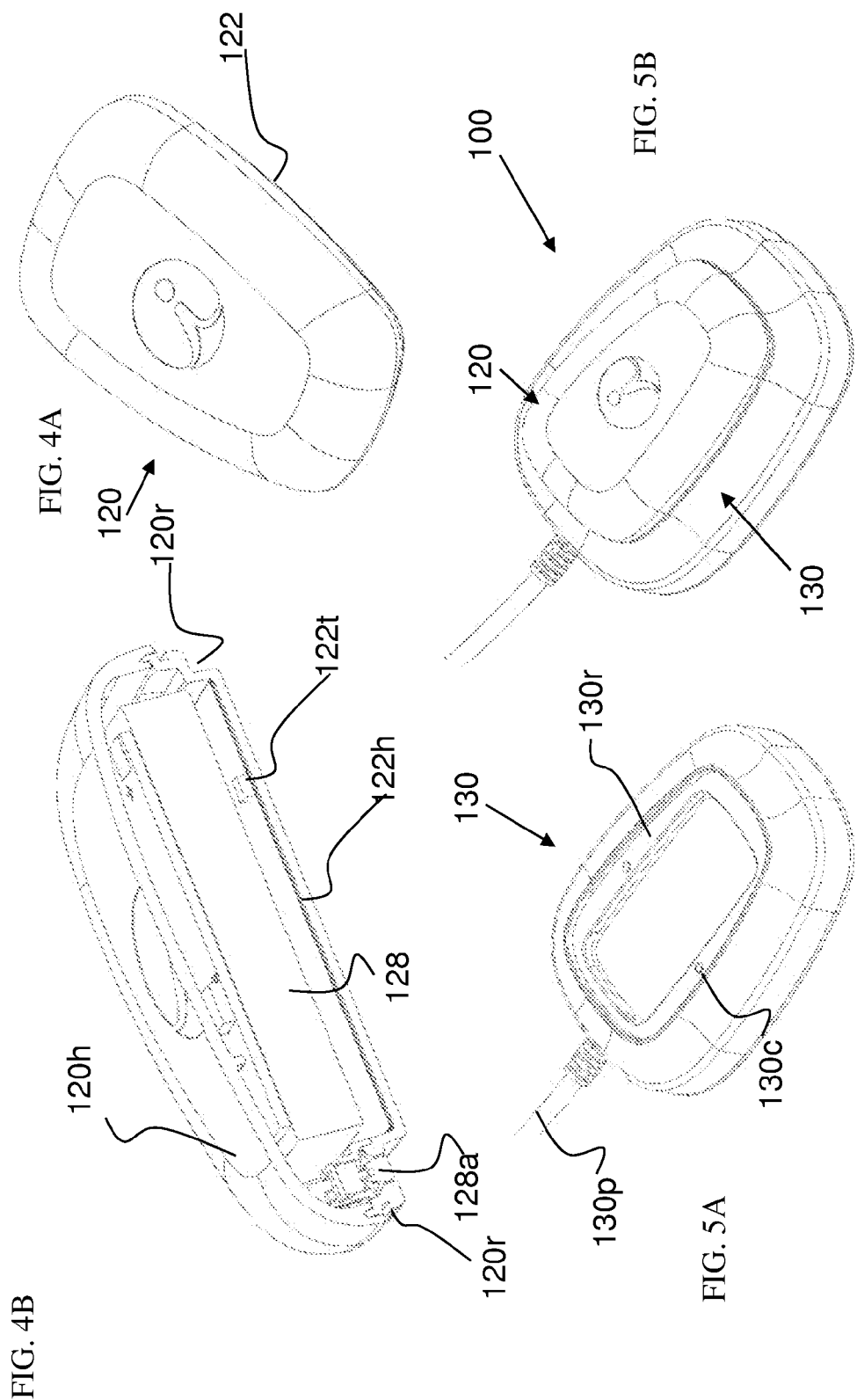

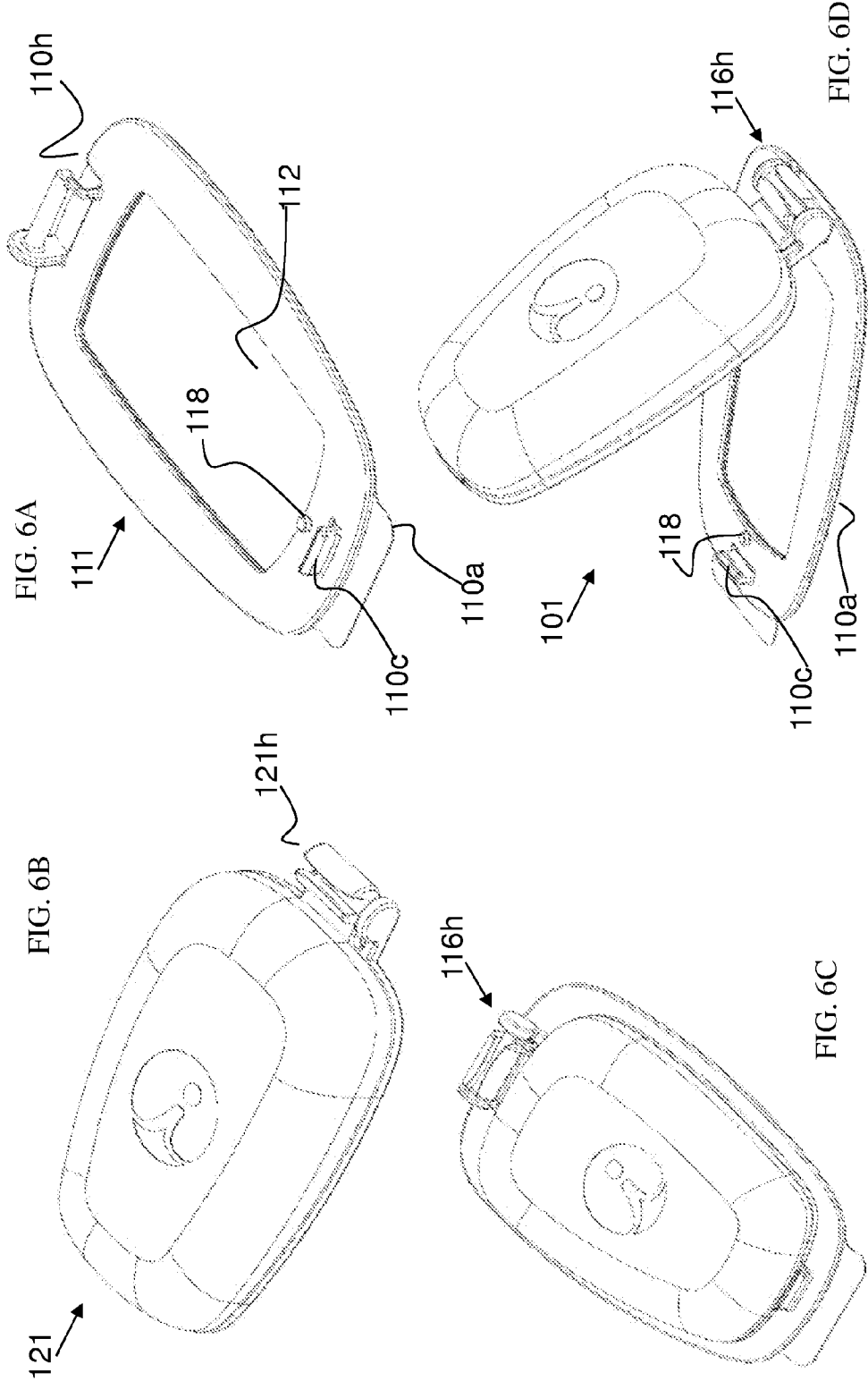

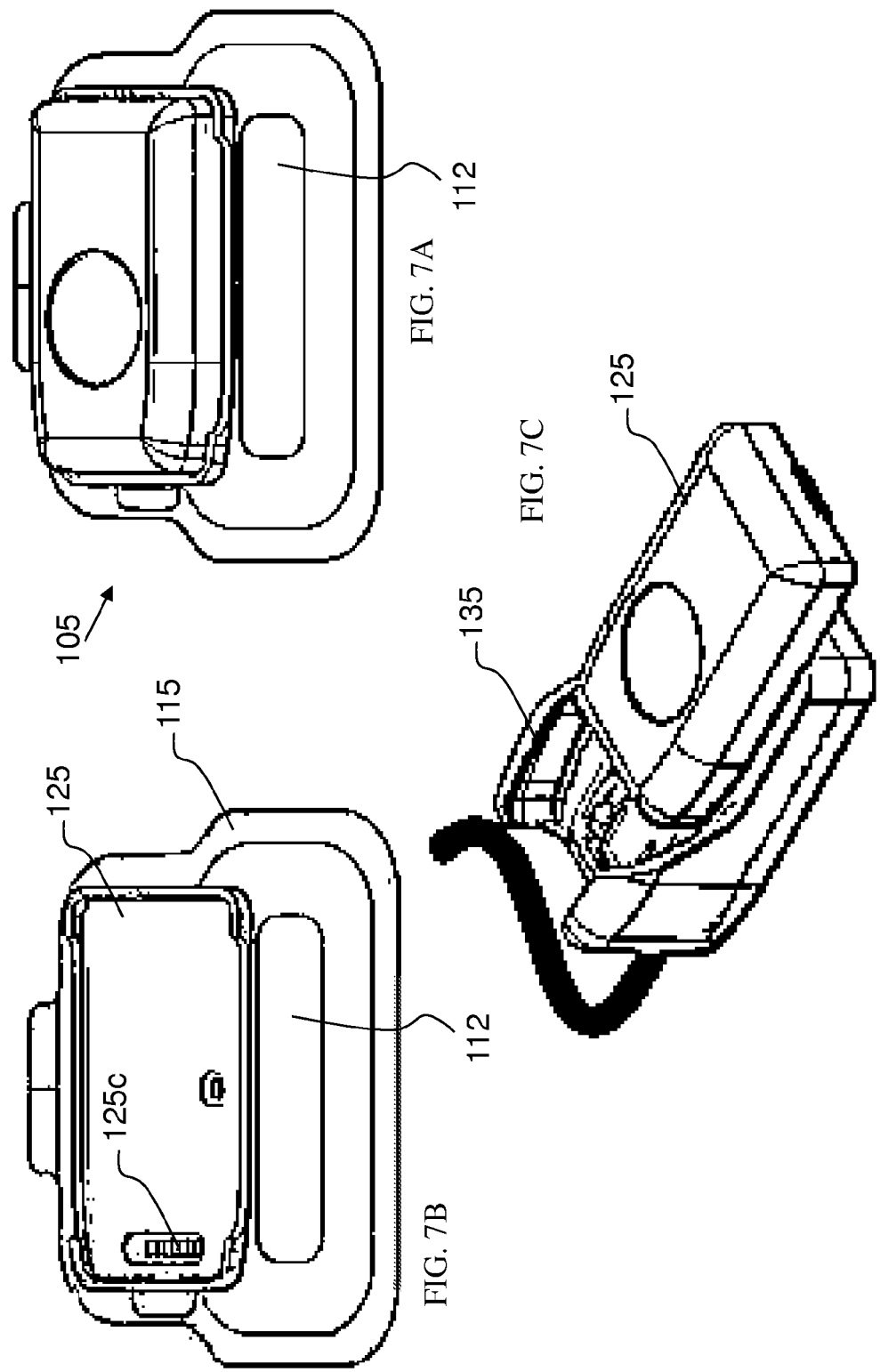

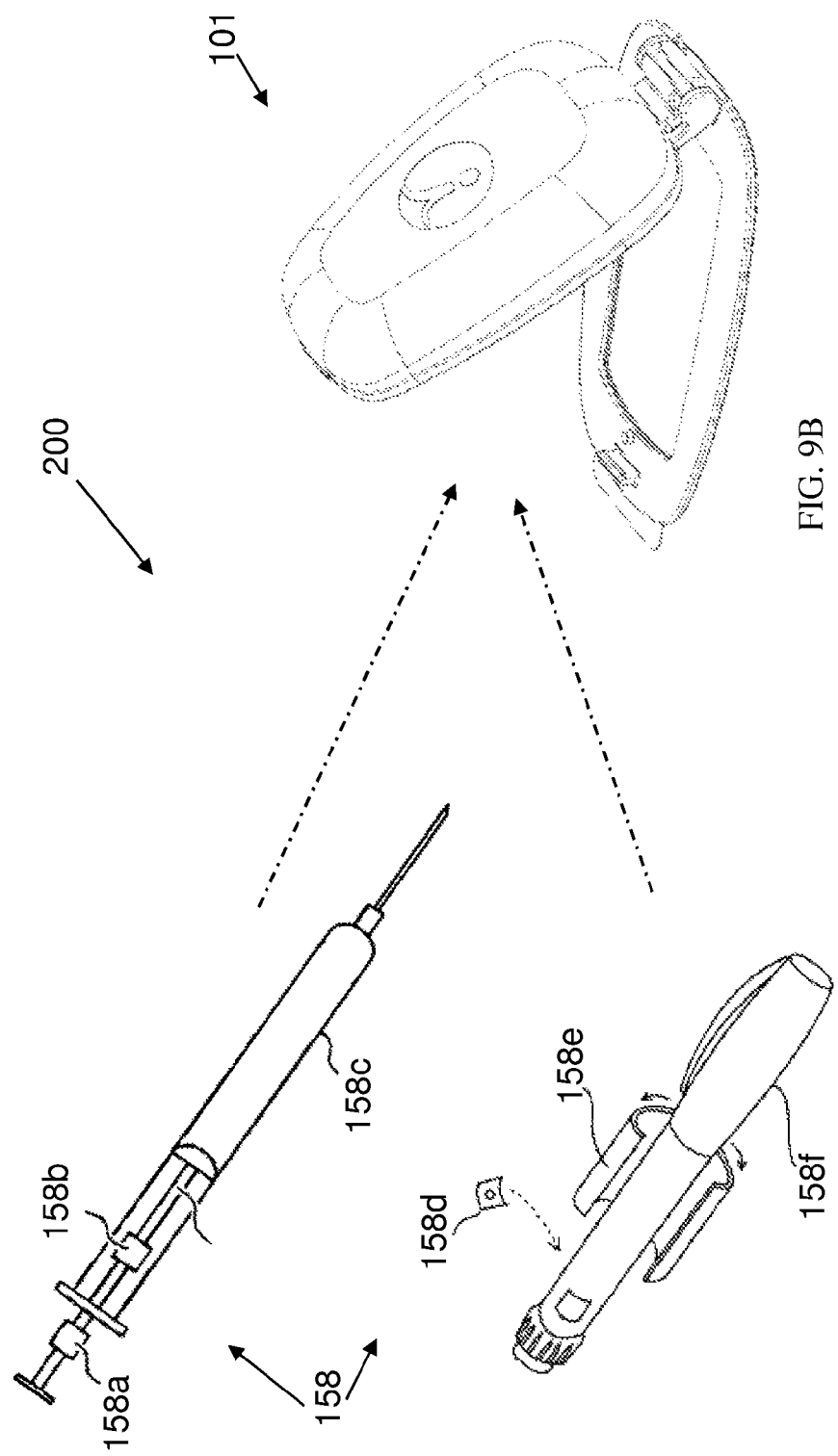

DEVICE, SYSTEM AND METHOD FOR FACILITATING SYRINGE BASED DRUG DELIVERY AND MANAGEMENT THEREOF

CROSS-REFERENCE TO RELATED APPLICATIONS

This application is a U.S. National Phase Application under 35 U.S.C. 371 of International Application No. PCT/IB2012/052335, which has an international filing date of May 10, 2012, and which claims the benefit of priority from U.S. Provisional Patent Application No. 61/484,457, filed on May 10, 2011, and U.S. Provisional Patent Application No. 61/598,127, filed on Feb. 13, 2012, which applications are incorporated herein by reference in their entirety.

FIELD OF THE INVENTION

The present invention relates to a device, system and a method for optimizing syringe based drug delivery profile with a treatment element and in particular, to such a device, system and method in which optimization is based on a plurality of data that directly and/or indirectly affect the optimization of the drug delivery profile.

BACKGROUND OF THE INVENTION

Various illnesses and disorders lead to situations that require continuous and tight control of systemic metabolic processes. As a result of the disease state it is difficult to control or predict the vast reaching systemic metabolic processes involved, where it is particularly difficult to predict the affects of one aspect of disease state on other aspects. However, such control is sought after to ensure the proper functioning of the body in all its systems.

Diabetes is perhaps the most well known illness that requires such close control of a systemic metabolic process. Control of diabetes and in particular the balance between blood sugar and insulin levels has far reaching and often lethal consequences if such control is lost. Systemic metabolic control for individuals suffering from diabetes has improved over the years with increased awareness, various systems and close monitoring of blood glucose levels, automatic drug delivery pumps and similar analyte and drug delivery systems that have been developed. However the systemic solutions such as an electronic artificial pancreas or close looped diabetes control system continues to elude us as a single point solution has yet to be found, particularly because of the human factors involved in control of the metabolic process involved with diabetes.

Furthermore such an automatic close loop system is only available to a small portion of the diabetic population. Such system is not available to the majority of diabetics primarily due to the cost involved in such a system. Most diabetics use syringe and/or injection pen based drug delivery systems for both basal and/or bolus insulin drug delivery.

There are many known metabolic processes having effect on diabetics include for example food intake, exercise, sleep, cardiovascular system, blood pressure, and involve both intrinsic biological processes, anatomical disposition, and human behavioral factors, a combination of factors that are not readily controllable, even if a closed loop system is available.

In many instances, diabetics require insulin injection around the clock to maintain proper blood glucose levels. Two major types of insulin may be administered—"long acting" insulin, that provides the basal insulin rate needed for keeping the blood glucose levels in the desired range for stretches of time for example, between meals and overnight and sometimes throughout a single day, a number of days or even a week. The basal, "slow acting", type of insulin does not have to rapidly reach the patient's circulatory system in order to take effect. The second type of insulin, is a short "rapid-acting", "bolus", insulin that is injected in relation to caloric intake or a meal and provides an amount of insulin for matching a dose of carbohydrates consumed by the patient. As its name suggests, "fast acting" insulin generally needs to reach the metabolic system quickly in order to take part in the metabolic process in a timely fashion, so as to avoid unwanted extreme situations.

When a patient consumes food, his or her levels of glucose rises which requires a metabolic reaction to offset the glucose rise, in diabetics this is achieved by administrating insulin, so as to maintain homeostasis or balance of blood glucose levels. The vast majority of the diabetic population utilized syringe based drug delivery devices to administer insulin so as to maintain blood glucose homeostasis. Unfortunately, existing "rapid acting" insulin currently in use with many conventional subcutaneous injection devices, including injection-ports, are incapable of quickly matching or preventing the rise of blood glucose, leading to metabolic imbalance due to lack of matching. Similarly, delay in such matching may also be experienced when "rapid-acting" insulin is administered.

Some of the reasons for this delay include a lag in the absorption of insulin from the injection site and the time it takes for complex insulin molecules to break down into monomers.

Additionally, since blood glucose levels rise shortly following the meal, the delay in matching insulin to the rising levels causes post-prandial hyperglycemic events (i.e., when levels of blood glucose are above normal) to occur. Further, occasionally after a certain period of time passes (e.g., 2-3 hours) after a meal, the blood glucose levels drop while the administered meal-time insulin concentration in the blood is rising, followed by the peak of the systemic insulin effect and may result in causing hypoglycemic events (i.e., when levels of blood glucose are below normal) to occur. Both hyperglycemic and hypoglycemic events are highly undesirable, and are indicative of a metabolic mismatch or imbalance in the systemic metabolic processes.

Other factors taking effect in the systemic metabolic process, include blood perfusion. Particularly local blood perfusion at the insulin injection region/site shows large variability, from one site to the other. Amongst other parameters, an important factor affecting blood perfusion includes ambient temperature. Ambient temperature is believed to be an important factor in the large variations to the delay of the peak of time profile of the insulin action. Such variations in the insulin peak action period further increase the variability in the blood glucose level, leading to metabolic imbalance.

Other factors that play into the systemic metabolic process include local affects at the injection site. For example, it is known that certain drugs including insulin are growth hormones. These drugs when injected several times at the same location can cause local cell growth, causing Lipohypertrophy. Therefore continuous insulin injection at a single injection site for extended period of time, for example several times per day or over several days, may lead to Lipohypertrophy. Increased local blood perfusion at the injection site to promote drug uptake to the circulatory system may reduce unwanted Lipohypertrophy of the injection site.

Other factors having a marked affect on the systemic metabolic process of diabetics include diet and/or food intake and level of exercise. Both factors have great affect on the systemic metabolic process and contribute greatly to the type of insulin to delivery, the required insulin dose, blood perfusion and likelihood of experiencing hyperglycemic and/or hypoglycemic events.

To date, despite numerous advances in the type of insulin drugs available to diabetics, continuous glucose monitoring devices, automatic drug delivery systems and pumps, closed looped monitoring, the sought after balance in the systemic metabolic control eludes many diabetics. This is largely believed to be a direct result of individual human factors, such as incorrect dosage, wrong drug type, inappropriate care of the drug itself (exposure), inactivity, unpredictable eating habits, and the like, are largely unpredictable.

Most insulin treated diabetics use injection and/or syringe based devices on a daily basis, they sometime use more than just one injection device to administer their insulin dose, even a single dose. They can and often use more than one blood glucose meter to measure their blood glucose levels before administering insulin. While there are new developments directed to capture daily diabetic behavior and parameters which can be used to optimize treatment, this human behavior is largely unpredictable, makes it difficult to track all the devices that are used by patients on a daily basis.

Therefore due to the non-predictable nature of the human factor and its involvement in the systemic metabolic process governing diabetes a different approach is required that will offset or attempt to offset at least some of the human factors involved, to try to maintain a blood glucose balance.

SUMMARY OF THE INVENTION

There is an unmet need for, and it would be highly useful to have, a drug delivery optimizing device, system and method that provides for optimizing the drug delivery profile, and in particular optimizing insulin drug delivery to diabetics.

It is a further objective of the present invention to provide a device that acts as a single focal point device that is conveniently attached to the diabetic patient on a daily basis throughout the day that can be used to collect all the data from the various devices a patient is using and optimize treatment.

A preferred embodiment of the present invention overcomes the deficiencies of the background art by providing a syringe based drug delivery optimizing device, system and method that provides for maintaining blood glucose homeostasis in diabetics by optimizing the drug delivery profile of insulin administered with a syringe based device. Most preferably balance and drug delivery optimization is provided by sensing, recording, communicating, and processing (integrating) and accounting for a plurality of data types and events that have a direct and/or indirect affect on the systemic metabolism and drug delivery of insulin. Most preferably an optimization protocol is abstracted with the drug delivery device and is based on the plurality of data types and events associated and communicated with the syringe based drug delivery optimizer of the present invention.

Most preferably the data utilized to optimize syringe based drug delivery include syringe injection events and associated medicament data, user's level of physical activity, meal detection status and physiological conditions (local and/or systemic).

A preferred embodiment of the present invention further provides a drug delivery optimizer that provides for minimizing risk of localized Lipohypertrophy at the injection site by comprising a single use period protection means.

Most preferably according to an optional embodiment the present invention provides a system for optimizing syringe based drug delivery by tracking and recording a plurality of data points relevant to direct and/or indirect blood glucose level of a diabetic, the system comprising drug delivery optimizer that is associated with a mobile communication device and/or HUB and further able to communicate with a plurality of optional auxiliary devices.

Therefore, it is desirable to provide a system and a method that provides efficient and rapid injection and absorption of the drug to the circulatory system when the drug is injected with a syringe based drug delivery device, for example a syringe, injection pen, or injection-port.

In particular, optional embodiment of the present invention provide a device, system and a method for optimizing drug delivery of syringe based injection of insulin that may be distinguish between injections of the various insulin types for example including, long acting insulin, short acting insulin, or mixed type insulin. Most preferably, while optimizing the transfer of insulin into the blood to maintain normal levels of blood glucose and prevent or reduce hyperglycemic and hypoglycemic events while limiting or preventing Lipohypertrophy at the injection site.

Within the context of this application the term "manual drug delivery" is to refer to non-automatic, syringe based, drug delivery performed with a syringe or injection pen or the like drug delivery.

Within the context of this application the term "single use" is interchangeable with the terms "single use time frame" or "single use period" or "single use period protection" refer to mechanical, electronic, or the like means utilized to ensure that a disposable unit and/or portion intended for single use is rendered non-operational and/or non-functional beyond the single user period intended for the device, unit, member or portion. Optionally and preferably a single use period protection utilized is defined according to the single use item. For example a disposable injection site unit according to the present invention may have a single use period of 24 hours while the single use period of disposable injection port according to an optional embodiment of the present invention may be defined to have a single use period of up to 3 days. Optionally the single use period protection means including mechanical and/or electronic means may be disposed on the single use and/or disposable member itself or by way of interaction (mechanical or electronic) with other non-disposable members. Optionally single use period protection means may for example include but is not limited to mechanical integrity of housings, connectors, adhesive, electrical contacts, electrical communication, time based interactions, or the like.

Within the context of this application the term "HUB" or "mobile communication device" refers to any device comprising a processor, communication capabilities and a user interface that may interchangeably be used with any of the terms for example including but not limited to server, smart-phone, mobile telephone, cellular telephone, Personal Data Assistant ('PDA'), computer, laptop, mobile computer or the like as is known and accepted as a term of art.

Optionally and most preferably the present invention relates to systems, devices and methods for injecting drug(s), substances and/or chemicals into a patient having a tissue treatment element for improving effectiveness of drug delivery upon injection. The device, according to some embodiments of the present invention, provides for a device for improving performance of drug delivery by injections with syringe based drug delivery. Optionally, some embodiments of the present invention provide for a device that further provides an additional treatment to a tissue region where the drug is delivered. The treatment can be utilized to improve drug delivery process by improving the drug's pharmacokinetic ("PK") and/or pharmacodynamic ("PD") profile.

Within the context of this application the term "treatment' and/or "treatment element" is to refer to any treatment type or a combination of treatment types that may be applied to an injection area to most preferably optimize drug delivery profile by directly or indirectly improving the delivery and absorption of the drug, for example insulin, to improve the drug's pharmacokinetic and for pharmacodynamic profile, optionally and preferably by improving vasodilatation of the tissue about the injection site. A treatment element and/or treatment or combination of treatment elements may come in various forms, for example including but not limited to an analgesic, vasodilator, or the like. Optionally, the treatment may be any form of treatment that leads to an improved vasodilatation of the tissue in and about the injection site, where the treatment, may for example include but is not limited to, exposing the tissue region to an energy, radiation, heat, mechanical vibrations, suction, massaging, acoustic stimulation, electrical stimulation, injection of an additional substance(s), or any combination of the above to improve drug's pharmacokinetic ('PK') and for pharmacodynamic ('PD') profile. Optionally an applied treatment may induce vasodilatation through neural stimulation of the tissue around the drug injection site. The neural stimulation can be induced by thermal stimulation. The human neural response to thermal stimulation includes several mechanisms such as the Nociceptive Axon Reflex that induces vasodilatation among other effects.

Optionally, an induced neural response, such as the nociceptive axon reflex, also optionally induces widening of the capillary pores and increasing the capillary wall permeability. This effect is also significant for improving the absorption of the drug through the capillary wall.

Optionally and preferably a treatment and/or a treatment element may be provided and/or applied to the injection site before, during or after administration and/or injection of the drug.

Optionally and most preferably the treatment element is controllable and may be provided in the form of a heater. Most preferably a drug's temperature sensitivity can be accounted for so as to avoid protein denaturisation.

In some embodiments, the delivered drug is insulin. Insulin is a temperature-sensitive protein. Thus, to avoid damage to insulin during the treatment protocol, heat can be limited so as to ensure efficacy of the delivered drug. The treatment protocol can be configured to control the temperature or the location of the treatment delivery site so as to not damage the drug. For instance, heating some types of insulin above 37° C. (degree Celsius) might damage it. Thus, the tissue around the injection site can be heated to induce the required neural response without heating the insulin itself above 37° C. For example heating the tissue at a distance of 10 mm around the injection site to 38.5° C. provides a significant vasodilatation without heating the injected insulin above 37° C. Another example of an optional treatment protocol by way of heat, may be heating the tissue at a distance of 10 mm around the injection site to 38° C. and in relation to that heating at a distance of 15 mm around the injection site to 40° C. to provide a significant vasodilatation without heating the injected insulin above 37° C. Another example of an optional treatment protocol by way of heat, may be achieved by modifying the temporal profile of heating to a certain temperature that provides a significant vasodilatation without heating the injected insulin above the limiting temperature which can be for example 37° C. Another example of an optional treatment protocol by way of heat, may be a combination of heating to a lower temperature for example about 38° C. in combination of providing another stimulation in relation to that, for example applying electrical stimulation, which will result in a desired tissue response without exposing the drug to a temperature over a limit temperature of about 37° C.

An optional insulin delivery optimization protocol for improving clinical outcome of a diabetic patient may be obtained by combining injection of rapid acting insulin analog with heating the skin around and above the injection site to about 37-42° C. in a way that combines spatial and temporal heat profiles with optionally other stimulations and applied to the skin area in relation to the injection, so that the injected drug is not exposed to a temperature exceeding a limiting temperature which can be for example about 37° C. This optional optimization protocol may be configured to provide a significant improvement of the insulin PK and PD without heating the injected insulin above about 37° C.

A preferred embodiment of the present invention provides a drug delivery optimizing device, (herein interchangeably referred to as "optimizer") and associated system and method of use, provided for optimizing the drug delivery profile, PK and PD, for a syringe based drug delivery device.

Optionally and preferably optimization of drug delivery may be provided with at least one or more optional treatment elements. Optionally and preferably the treatment element may be provided in the form of a heating element. Optional and most preferably heating an injection area improves the administration of drug, for example insulin.

Most preferably the optimizing device includes a treatment element with a controllable heating element in temperature communicative contact with the tissue adjacent to the drug injection site. The controllable heating element is configured to heat the tissue adjacent to the drug injection site to a controllable temperature but does not heat the injected drug above a predetermined limiting temperature, above which degradation of the injected drug may occur.

An optional embodiment of the present invention relates to a method for treating a patient using a treatment device including a pen injector and a treatment element having a controllable treatment element. The method includes injecting a drug into a tissue on the body of the patient at a drug injection site using the pen injector; and using the treatment element, applying a treatment to the drug injection site before, during or after the injecting.

Optionally and most preferably, meal detection may be provided by an intrinsic meal detection sensor, for example provided in the form of a microphone detection chewing sounds and/or gastro-intestinal sounds.

Optionally, meal detection may be provided in the form of a dedicated meal detection auxiliary device capable of communicating with the drug delivery optimizer according to an optional embodiment of the present invention.

Optionally, meal detection sensor or device may comprise at least one and more preferably at least two or more sensors for example including but not limited to acoustic sensor, microphone, pressure sensor, oral analyte sensor, glucose sensor, gyroscope sensor, volumetric sensor, accelerometer sensor, inertial sensor, any combination thereof or the like as is known and accepted in the art.

Optionally and preferably, individual sensors may be adept at detecting a particular state that may be associated with a meal.

For example, a volumetric sensor may sense the changing volume of the Gastrointestinal system to determine the meal state while differentiating between fluid intake and solid intake.

For example, a glucose monitor may identify the rate of change of oral glucose levels indicating a meal.

For example, a salivary analyte sensor may sense the increase in salivary amylase in the saliva to infer a meal state.

For example, a gyroscopic sensor and/or an inertial sensor may sense the movement of the upper and lower jaw with respect to one another.

For example, a microphone may sense chewing sounds.

For example, a pressure sensor may detect pressure changes within the oral cavity, or along the surface of at least one tooth or at least two teeth. For example, a combination of a microphone to detect chewing sounds optionally together with Gastrointestinal sound together with an inertial sensors that may detect a sitting position may be used together to identify a sitting meal event.

Optionally, the optimizer according to the present invention comprises a physical activity sensor and/or external auxiliary monitor. Most preferably, physical activity sensor may be provided as an intrinsic sensor forming part of the optimizer according to the present invention. Optionally, activity sensor may be realized as an external auxiliary device.

Optional physical activity sensor may provide for determining and/or calculating calorie burn or expenditure of a user. Optionally and preferably, physical activity may for example include a motion sensor to detect motion of the user and in response, an altitude sensor to detect a change in altitude of the user, and circuitry to infer physical activity of a user.

An optional embodiment of the present invention relates to a method for treating a patient using a treatment device placed over an injection site or an injection port, while collecting information on the injected drug at the time of injections with option to provide feedback to the user, such as alerts on missed injections. Such treatment device may include a disposable element and a reusable element adapted to operate with a pen injector, a syringe or an injection port. Optionally and preferably the reusable part of the treatment element may be adapted to additionally perform and optionally provide for optimizing a treatment comprising at least one or a combination for example including but not limited to: recording daily injection events made by plurality of injection devices, measure the size of the subcutaneous drug depot over time, record daily activity and calorie burn rate associated with user activity, record and optionally use information on meal events, measure and use information about local blood perfusion, communicate with peripheral and or mobile devices, used by the diabetic during the day to measure blood glucose levels, calculate and record food carbohydrate content based on food photos with respect to a known reference, calculate required insulin doses, transmit captured data in real time or at one or more times during the day to a center to get feedback that may be used to optimize daily treatment, during daily activity of a diabetic. Either of the reusable or disposable parts may optionally and preferably comprise controllable treatment element. The method includes injecting a drug into a tissue on the body of the patient at a drug injection site using a pen injector; a syringe or an injection port and using the treatment element, to apply a treatment to the drug injection site before, during or after the injecting.

For example, such device for providing treatment to the tissue at the injection site comprising a disposable unit and a reusable unit that may be used daily as described herein: the reusable unit is charged overnight and a user takes the charged reusable unit from the base station/charger as he/she wakes up. User connects the reusable unit to a new disposable unit and using the adhesive layer of the disposable unit affixes the assembly on a preferred skin area to be used for meal time bolus drug injections. From that time the unit while having motion sensors and memory and processor can calculate and record user calorie burn. With injection device (pen or syringe) having RFID and EEPROM with optionally electronic circuit that converts mechanical adjustments made for adjusting the amount of injected drug to an electronic signal readable by the reusable unit while in proximity to the reusable unit, the reusable unit detects the presence of injection device, record the injection event with all relevant data (drug type, LOT number and expiration date, drug exposure to elevated temperatures, date of first use, setting of amount of drug to be injected, date & time of injection), verify that the injection event corresponds to meal time drug injection and further verify that injection amount corresponds to recommended dose communicated to the reusable unit from a dose calculator, tracks the local blood perfusion and subcutaneous drug depot and optimizes treatment applied to the tissue at the vicinity of the drug depot to optimize drug effect in respect to the desired disease treatment. With diabetics, and meal time insulin injections, optimizing blood glucose levels post meals. Transmission of signal to get response from RFID on injection devices can be triggered based on motion sensors and/or meal detection sensors in the reusable unit, and or on mechanical movement applied to the reusable unit before injection in order to prepare it for injection and applying treatment, and/or in response to proximity of the injection device. If meal detection sensors are included in the reusable unit, pretreatment may be applied to the tissue area even before injection, and alerts may be provided to the user in case of missed meal time injections. Data from any injection device used by the user having at least RFID tag, & EEPROM, at the time period when the reusable unit was affixed to the user skin is recorded. Hence the user is not limited to using only one injection device but may use a plurality of such devices, while having all the data captured and recorded in the reusable units memory, with respect to all syringe based injection devices used. Such data may be downloaded and/or uploaded or otherwise communicated to a mobile device, a computer or to the internet, optionally such communication may be performed when the reusable unit is removed and/or disassociated from the disposable unit (and user) and associated with and/or placed on base station to be recharged; optionally if the reusable unit includes a transponder, transmit the data wirelessly to a mobile device.

Optionally, injection devices RFID tag and electronics may be embedded in the injection device in the case of devices to be used until the drug reservoir is emptied, or a separate part mounted on reusable injection devices, or embedded into drug reservoir to be used in reusable injection devices.

Optionally, in an event of conflicting data such as non-meal time drug injected at a treatment location, the reusable unit may alert the user or avoid treatment application. Similarly in the event of meal time drug injected at a distant tissue location relative to the treatment site, such data may be conveyed to the user by audible or visual display.

Further with this example if the reusable unit is mechanically moved to reveal injection area at the disposable unit or in the event of injection device connected to the injection port the reusable unit registers the injection event and drug data in case of meal time insulin injection, treatment is applied in case of non-meal-time insulin detected by the reusable unit, treatment is not applied and conflict event is registered in the reusable unit memory with optional alert to the user.

Most preferably at the end of a single use period the user removes the assembly off the skin area, disconnects the reusable unit, placing it on the base station to be recharged and communicate stored data while disposing of the disposable unit.

An optional embodiment of the system of the present invention may provide for identifying at least one or more emergency and/or ambulatory situations, for example, including but not limited to an ambulatory hypoglycemic event, ambulatory hyperglycemic event, fall, accident, loss of function, cardiac arrest, loss of consciences, elevated heart rate, elevated blood pressure, or the like, potential emergency and/or ambulatory events, and communicating such events to at least one or more authorized personnel or individual for example, including but not limited to a next of kin, health care provider, dedicated call center, remote control center, emergency service providers, ambulatory services, medical services provider, health services provider or the like authorized individual or service.

Most preferably a system according to the present invention, providing for the identification of emergency situations, comprises an optimizer drug delivery device that is associated with a mobile communication device and/or HUB.

Most preferably the sensor module included in the optimizer drug provides for sensing and/or identifying different ambulatory and/or emergency situations, the controller and/or processor provides for processing such events, for example by comparing a sensed event to a predefined threshold, the communication module provides for communicating the event either directly or via an associated mobile communication device and/or HUB. Optionally when the event is communicated it may include relevant data stored in the optimizer, for example, including but not limited to the identified event, automated description of the event, data corresponding to the event, data within a timeframe of the event, full data dump available, any available data analysis, any combination thereof or the like.

For example, a physical activity sensor including and/or provided in the form of an accelerometer may be used to identify an event of extreme acceleration, well above a threshold, such as a fall, accident, car accident, fall due to loss of consciences or the like, that is communicated to a dedicated call center to take appropriate action. Optionally when communicating the event details of the event and/or suspected event is communicated with a 12 hour data dump, so as to identify and hyperglycemic or hypoglycemic events leading to a fall due to loss of consciousness.

For example, an event of elevated heart rate, heart attack, elevated or spike in blood pressure, elevated core temperature, may be sensed with a physiological sensor disposed in the optimizer sensor module. Such events identified by analysis with the optimizer's processor may be communicated directly to ambulatory services. Optionally combined events such as a fall due to hyperglycemia and cardiac arrhythmia may be sensed by a combination of sensors disposed with the optimizer of the present invention and communicated with an associated mobile communication device or HUB via a communication port.

An optional embodiment according to the present invention provides a device for facilitating drug delivery with syringe based devices, wherein the device optimizes the delivery of the injected drug, records user activity and data relative to drug injections while the drug is administered, the device comprises:

a disposable unit configured for a single use period characterized in that the disposable unit may be rendered non-functional after the single use period; the disposable unit comprising a lower surface having a biocompatible adhesive with removable laminate for coupling the disposable unit over an area of skin defining an injection area; the disposable unit having at least one connector for coupling with a reusable unit and an activating member configured to activate the reusable unit;

the reusable unit having electronics comprising: control module, memory module, power supply module, communication module, contactless communication module, treatment element module and sensor module; wherein the power supply module comprises a rechargeable energy source that may be replenished with a base station unit for charging the power supply.

Optionally, the disposable unit defines an injection area of about 2 cm by 4 cm. Optionally, the disposable unit defines an injection area having any geometric shape.

Optionally, the activating member disposed about the disposable unit may be electronically or mechanically configured to interact and/or couple with a corresponding activation member disposed about the reusable unit, both members providing for activating or deactivating at least one or more functions of the optimizing device.

Optionally and most preferably, the device may be configured for a single use period about any portion of the disposable member, for example, including but not limited to adhesive layer, electronics, coupling members, and a combination thereof.

Optionally, the single use period may be configured to be from about one day or up to three days.

Optionally, the single use period may be established by way of communication and/or interaction between any member or portion of the disposable unit and reusable unit.

Optionally, the single use period may be configured according to number of injections administered within the drug delivery injection site.

Optionally, the number of injections may be at least 4 injections.

Optionally, the disposable unit may be configured for use as a drug delivery port having a single use cannula over the injection area and a single use period of about three days.

Most preferably, the device comprises at least one connector for connecting the disposable unit to the reusable unit.

Optionally, the connector may be provided in the form of a hinge comprising two hinge members that may be coupled or decoupled with one another including (male/female) a first member (male) provided on the disposable unit and a second member (female) provided on the reusable unit.

Optionally and preferably, associating and/or disassociating the two hinge member with one another may only be accomplished while the disposable unit is not coupled to the skin over an injection site. Optionally wherein associating and disassociating the two hinge members may be only possible when the first member and the second member are positioned at a reflex angle relative to one another, for example 270 degrees formed between the disposable unit and the reusable unit.

Most preferably, the reusable portion and disposable unit may be moved relative to one another to assume a plurality of configurations including an open configuration and a closed configuration.

Optionally, the disposable unit may comprise two surfaces that are coupled about a first end having a hinge member connecting the two surfaces. Most preferably the two surfaces include a lower surface comprising a laminate covering a biocompatible adhesive provided for association with a user's skin defining an injection area; and an upper surface maneuverable relative to the lower surface about the hinge; and wherein the upper surface may be configured to securely associate/couple with and receive the reusable portion.

Most preferably, the base station unit may be adapted for receiving and securely associating with the reusable unit. Most preferably the base station comprises a power supply module provided for recharging/powering the reusable unit and a communication module provided for communicating and data exchange with the reusable unit.

Optionally, the base station unit charges the reusable unit via electrical contacts or by induction.

Optionally and preferably, the sensor module of the reusable unit may comprise a motion sensor detecting motion of a syringe based drug delivery device in the vicinity of the reusable portion.

Optionally, the reusable portion's communication module provides for communicating and interfacing with at least one or more auxiliary devices for example including but not limited to mobile communication device, meal detection devices, blood glucose monitor, physical activity detector, syringe, drug delivery pen, caloric intake calculator, food analysis device, basal only pump, bolus only pump, blood pressure and pulse monitor, any combination thereof.

Optionally, an auxiliary physical activity monitoring device may for example include but is not limited to smart-shoes, pedometer, accelerometer, fitness monitoring device, or the like as is known in the art.

Optionally, the communication module of the reusable portion and base station may for example include but is not limited to: contactless communication, near field communication, wireless communication, cellular communication, RFID based communication, Bluetooth, WiFi, ZigBee, optical communication, piezoelectric and/or acoustic communication.

Optionally and most preferably, the contactless communication module disposed in the reusable unit may be adapted for interfacing with a syringe based drug delivery device fit with at least one or more corresponding contactless electronic identification circuitry, for identifying at least one or more of the syringe based drug delivery devices, syringe contents, set drug dose dosage, drug's storage environment, any combination thereof of the like.

Most preferably, the sensor module of the reusable unit may comprise a meal detection sensor, for detecting a user's meal state, and a physical activity sensor for detecting a user's physical activity, posture, and positioning.

Optionally, the sensor module further comprises an impedance sensor for identifying drug delivery status, physiological sensor for identifying the user's physiological parameters.

Optionally, physiological parameter may for example include but is not limited to localized blood perfusion about the injection site.

Optionally, the meal detection sensor may be provided in the form of at least one microphone integrated with the reusable portion or the disposable portion.

Optionally, the sensor module may further comprise a treatment element for applying a treatment to a user, most preferably over the injection area, before, after or during a syringe based drug administration. Optionally and preferably the treatment element optimizes the drug delivery profile and improves the pharmacodynamic and pharmacokinetic drug profile.

An optional embodiment of the present invention provides a system for facilitating and managing drug delivery with a plurality of syringe based drug delivery devices, the system includes the drug delivery optimizing device according to optional embodiments of the present invention and at least one contactless electronic identification circuitry coupled or otherwise associated with at least one or more syringe based drug delivery device, for example a syringe or injection pen, for communication injection data and administered drug data.

Most preferably, the system may further communicate and/or interface with a mobile communication device therein facilitating communication with the drug delivery optimizer.

Optionally and preferably, the system may further comprise at least one or more auxiliary device. Optionally and preferably the auxiliary device may for example include but is not limited to: a meal detection device, blood glucose monitor, physical activity detector, syringe, drug delivery pen, caloric intake calculator, food analysis device, basal only pump, bolus only pump and blood pressure monitor.

Optionally, the system may further include a linked and/or associated and/or in fluid communication with a blood glucose monitor.

Optionally, the optimizer's reusable unit may provide for interfacing and/or communicating with the auxiliary devices, optionally and preferably for integrating and storing data provided from the individual auxiliary devices Optionally, the system may further communicate and/or interfaced with a HUB comprising hardware, dedicated software and/or applications for managing and optimizing drug delivery with the optimizing device according to an optional embodiment of the present invention.

Optionally, the HUB may be configured to download and/or pull data from the optimizer's reusable unit and thereafter flush the data.

Optionally, the HUB may be configured to provide the system's long term memory while the optimizer's reusable portion may be configured to provide the system's short term memory equivalent to a single use period.

Optionally, the short term memory may be flushed when the reusable portion may be charged with a charger unit.

Optionally, control of the reusable portion may be determined by analyzing data from the system's long term memory.

Optionally and preferably, the HUB may further provide for integrating and managing data from at least one or more auxiliary devices, for example, including but not limited to a meal detection device, blood glucose monitor, physical activity detector, syringe, drug delivery pen, caloric intake calculator, food analysis device, blood pressure monitor, basal only pump, bolus only pump, and any combination thereof.

An optional embodiment of the present invention provides a method for optimizing drug delivery with a syringe based drug delivery device, the method comprising:

Associating the drug delivery optimizer according to the present invention with a HUB, therein forming an optional system according to the present invention;

associating a plurality of auxiliary devices with the HUB;

communicating data from the plurality of auxiliary devices and drug delivery optimizer device to the HUB;

determining an optimization drug delivery protocol based on the data communicated to the HUB; and the HUB communicates the optimized drug delivery protocol to the drug delivery optimizer.

Optionally, the auxiliary devices may for example include but are not limited to a mobile communication device, meal detection devices, blood glucose monitor, physical activity detector, syringe, drug delivery pen, caloric intake calculator, food analysis device, blood pressure monitor, basal only pump, bolus only pump, any combination thereof or the like.

Optionally and preferably, the method further provides for the HUB to determine the metabolic parameters affecting the drug delivery and abstracting an optimized drug delivery treatment plan. Optionally the optimization plan may be abstracted relative to at least one goal. Optionally and preferably the goal may be maintaining a balanced blood glucose level reading.

An optional embodiment of the present invention provides a method for optimizing drug delivery with a drug delivery optimizer according to optional embodiments of the present invention, the method comprising:

coupling the optimizing device with a user for continuously recording user's daily activity, the physical activity sensor and meal event with the meal detection sensor;

continuously communicate with at least one or more auxiliary devices for obtaining supplementary data; and storing the auxiliary device data;

with each use of a drug delivery optimizer, interrogate the individual syringe based drug delivery device, (injection pen, syringe) both for bolus or basal drug delivery injections, to obtain syringe data including syringe identification, syringe parameters and data associated with the syringe contents; wherein the data exchange may be provided by the contactless communication module and wherein the communicated data may be stored in the memory module of the optimizing device, along with a date and time stamp; and communicate all obtained data to the optimizer device for controlling a treatment element provided to facilitate drug delivery.

An optional embodiment of the present invention provides a method for automatic activation of a drug delivery optimizer according to optional embodiments of the present invention when a meal event is detected, the method comprising:

detecting a meal event with the optimizer's intrinsic activity sensor and the meal detection sensor;

initiating a timer from detection of the meal time event and await a bolus injection in response to said sensed meal event;

if bolus injection is not sensed provide a reminder as necessary;

optimizer detects pending injection through contactless communication with syringe based drug delivery device (syringe, injection pen); and initiate drug delivery treatment protocol based on available data.

Optionally, prior to initiating the bolus timer, the optimizer may further comprise communicating with an auxiliary device to obtains blood glucose data and expected drug delivery dose. Optionally, the drug delivery dose may be communicated from an auxiliary food and/or caloric calculator.

Unless otherwise defined, all technical and scientific terms used herein have the same meaning as commonly understood by one of ordinary skill in the art to which this invention belongs. The materials, methods, and examples provided herein are illustrative only and not intended to be limiting. Implementation of the method and system of the present invention involves performing or completing certain selected tasks or steps manually, automatically, or a combination thereof.

Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Optionally, any device featuring a data processor and/or the ability to execute one or more instructions may be described as a computer, including but not limited to a PC (personal computer), a server, a minicomputer, a cellular telephone, a smart phone, a PDA (personal data assistant), a pager. Any two or more of such devices in communication with each other, and/or any computer in communication with any other computer, may optionally comprise a "computer network".

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2A-B are schematic illustrative diagrams of an exemplary drug delivery optimizing device comprising a disposable unit and a reusable unit, according to an optional embodiment of the present invention; FIG. 2A shows a closed configuration of the drug delivery optimizing device and FIG. 2B shows an open configuration of the drug delivery optimizing device;

FIGS. 3A-B are schematic illustrative diagrams of the disposable unit of an exemplary drug delivery optimizing device according to an optional embodiment of the present invention; FIG. 3A shows a closed configuration of the disposable unit and FIG. 3B shows an open configuration of the disposable unit;

FIGS. 4A-B are schematic illustrative diagrams of the reusable unit of an exemplary drug delivery optimizing device according to an optional embodiment of the present invention; FIG. 4A shows a perspective view of the reusable unit and FIG. 4B shows a cross sectional view of the reusable unit;

FIGS. 5A-B are schematic illustrative diagrams of the base station unit of an exemplary drug delivery optimizing device according to an optional embodiment of the present invention; FIG. 5A shows a perspective view of the base station unit and FIG. 5B shows the base station unit coupled with an optional reusable unit;

FIGS. 6A-D are schematic illustrative diagrams of an optional drug delivery optimizing device comprising a disposable unit and a reusable unit, according to an optional embodiment of the present invention; FIG. 6A shows a perspective view of the disposable unit; FIG. 6B shows a perspective view of the reusable unit; FIG. 6C shows a closed configuration of the drug delivery optimizing device and FIG. 6D shows an open configuration of the drug delivery optimizing device;

FIGS. 7A-C are schematic illustrative diagrams of an optional drug delivery optimizing device comprising a disposable unit and a reusable unit, according to an optional embodiment of the present invention;

FIG. 9B is a schematic illustrative diagram of a system according to an optional embodiment of the present invention as shown in FIG. 9A;

DETAILED DESCRIPTION OF THE INVENTION

The principles and operation of the present invention may be better understood with reference to the drawings and the accompanying description. The following figure reference labels are used throughout the description to refer to similarly functioning components are used throughout the specification hereinbelow.

100 Syringe based Drug Delivery Optimizer;
101 Hinged optimizer;
102 functional optimizing device;
104 charging optimizing device;
100P syringe based drug delivery port;
110 disposable unit;
110a adhesive surface;
110c disposable unit coupler;
110f disposable unit coupling frame;
110h disposable (male) hinge coupling portion;
110r reusable unit coupling recess;
110L lower member;
110U upper member;
111 hinged disposable unit;
112 injection site;
112C injection site cannula;
112P injection site port;
112U upper member injection site recess;
112L lower member injection site recess;
116 disposable integrated hinge;
116h split hinge assembly;
118 activating pin;
120 reusable unit;
120h reusable unit housing;
120i reusable unit human interface;
120P drug port reusable unit;
120r disposable unit coupling recess;
120S sensor module;
121 hinged reusable unit;
122 treatment element;
122h heating element;
122t thermistor;
123 physiological sensor;
124 physical activity sensor/monitor;
125 disposable unit with integrated heating member;
126 meal detection sensor;
127 impedance sensor;
128 reusable electronic module;
128a activation pin member recess;
128C controller module;
128M memory module;
128P power supply module;
128R contactless communication module;
128T communication module;
128U user interface module;
130 base station unit;
130r reusable unit coupling recess;
130c reusable unit contacts;
130p mains power;
132 base station controller;
134 base station power supply module;
135 base station;
136 base station memory module;
138 base station communication/transponder module;
150 auxiliary devices
151 Blood Glucose Monitor;
152 Basal or Bolus only Pump;
153 Insulin Dose Calculator;
154 Meal detecting device;
155 food analysis calculator;
156 Pulse/Blood Pressure device;
157 physical activity monitor;
158 Syringe based drug delivery device syringe/injection pen;
158a-e contactless communication tags;
159 mobile communication device;
160 System HUB;
200, 202 Drug Delivery Optimizer System;
210 Offline Data acquisition module.

Figure 1:
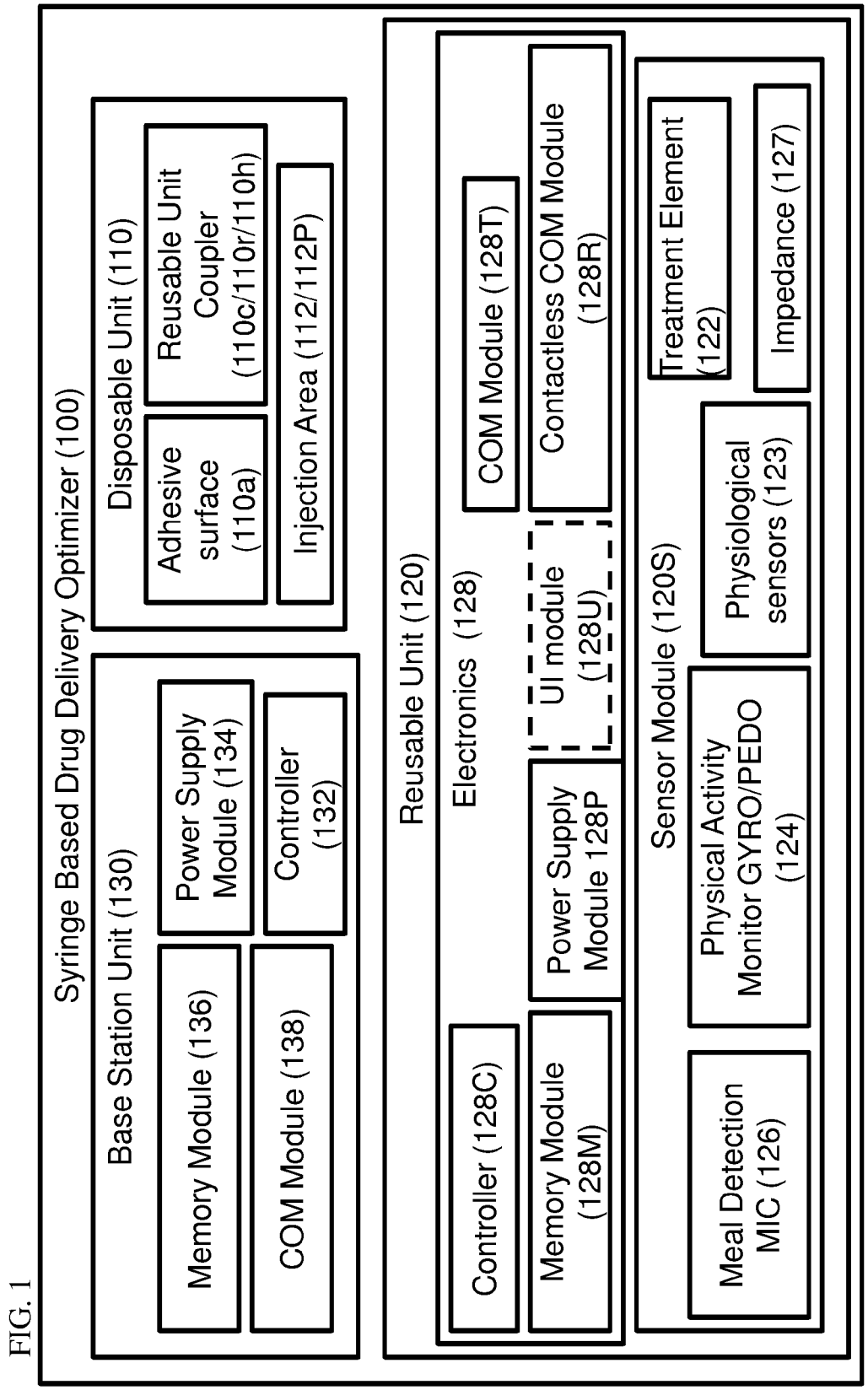
FIG. 1 is a schematic block diagram of a drug delivery optimizing device according to the present invention.

FIG. 1 shows a schematic block diagram of syringe based drug delivery optimizing device 100 provided for optimizing the drug delivery profile by optimizing the pharmacokinetic and pharmacodynamic properties of the administered drug. Most preferably optimizer 100 provides for facilitating timely absorption and metabolism of a manually administered drug, most preferably via a syringe or injection pen. Optimizer 100 provides for optimizing drug delivery by controllably applying heat over an injection area in relation to syringe based drug administration, while controlling the heating cycles and parameters among other and optionally based on a wide spectrum of user related data that affects the systemic metabolic process related the administered drug, for example insulin. Most preferably device 100 provides for proactive controlling of insulin metabolism by way of syringe based drug delivery therein, optimizing and therefore minimizing episodes of post prandial hyperglycemic and hypoglycemic events.

Most preferably device 100 optimizes insulin absorption by comprising at least one and more preferably two or more sensors and actuators configured to automatically and seamlessly provide data relating to user's meal status, meal timing, the timing of administered drug, drug dose, drug type, logging user activity, analyzing user physical activity, controlled heating of the injection area, any combination thereof or the like.

Most preferably device 100 may be placed over an injection site or an injection port and used for treating the tissue at the injection site, while collecting information on the injected drug at the time of injections with an option to provide feedback to the user, such as alerts on missed injections. Such treatment device may for example include a disposable element and a reusable element adapted to operate with a syringe based drug delivery device, for example, including but not limited to a pen injector, a syringe or an injection port, or the like as is known in the art. The reusable part of the treatment element may be adapted to additionally perform and optionally used to optimize treatment, one or a combination from: record daily injection events made by plurality of injection devices, measure the size of the subcutaneous drug depot over time, record daily activity and calorie burn of the user, record and optionally use information on meal events, measure and use information about local blood perfusion, communicate with peripheral and or mobile devices, used by the diabetic user over the day to measure blood glucose levels, calculate and record food carbohydrate content based on food photos with respect to a known reference, calculate required insulin doses, transmit captured data in real time or at one or more times during the day to a center to get feedback that can be used to optimize daily treatment, during daily activity of a diabetic. Optionally, either of the reusable and/or disposable parts may include the controllable treatment element. The method includes injecting a drug into a tissue on the body of the patient at a drug injection site using a pen injector; a syringe or an injection port and using the treatment element, applying a treatment to the drug injection site before, during or after the injecting Most preferably various configurations of device 100 may be configured to associate with a defined injection area for a single use period, for example a one day period, or up to a three day period.

Most preferably device 100 is configured such that device 100 is rendered non-functional over an injection area beyond the single use period.

Optimizing device 100 comprises a disposable unit 110, base station 130 and a reusable unit 120.

Disposable unit 110 may be provided in a plurality of optional configuration, all including at least one surface provided in the form of a single use pad that may be coupled to the user's skin surface therein defining an injection area 112 for a single use period. Optionally and preferably the length of a single use period is correlated and varies according to the configuration of disposable unit 110.

Disposable unit 110 comprises a first surface that provides for coupling to the user's skin with a biocompatible adhesive 110a. Most preferably prior to use, adhesive surface 110a is covered with a laminate that may be peeled to expose the adhesive surface prior to applying and coupling to the user's skin by pressing adhesive surface 110a onto the user's skin surface. Optionally and preferably the length of a single use period is correlated to the biocompatible adhesive 110a.

Most preferably disposable unit 110 is provided for coupling with reusable unit 120, to form a functional unit 102 over injection area 112, that functions to optimize syringe based drug delivery. Most preferably disposable unit may be coupled or otherwise associated with reusable unit 120 in a plurality of optional manners utilizing a plurality of optional couplers for example including but not limited to male/female coupler, hinge coupler, press fit coupling, pressure fit coupling, snap-fit couplers, latch-fit coupler, snap-in rail coupling, any combination thereof or the like.

Figure 8:
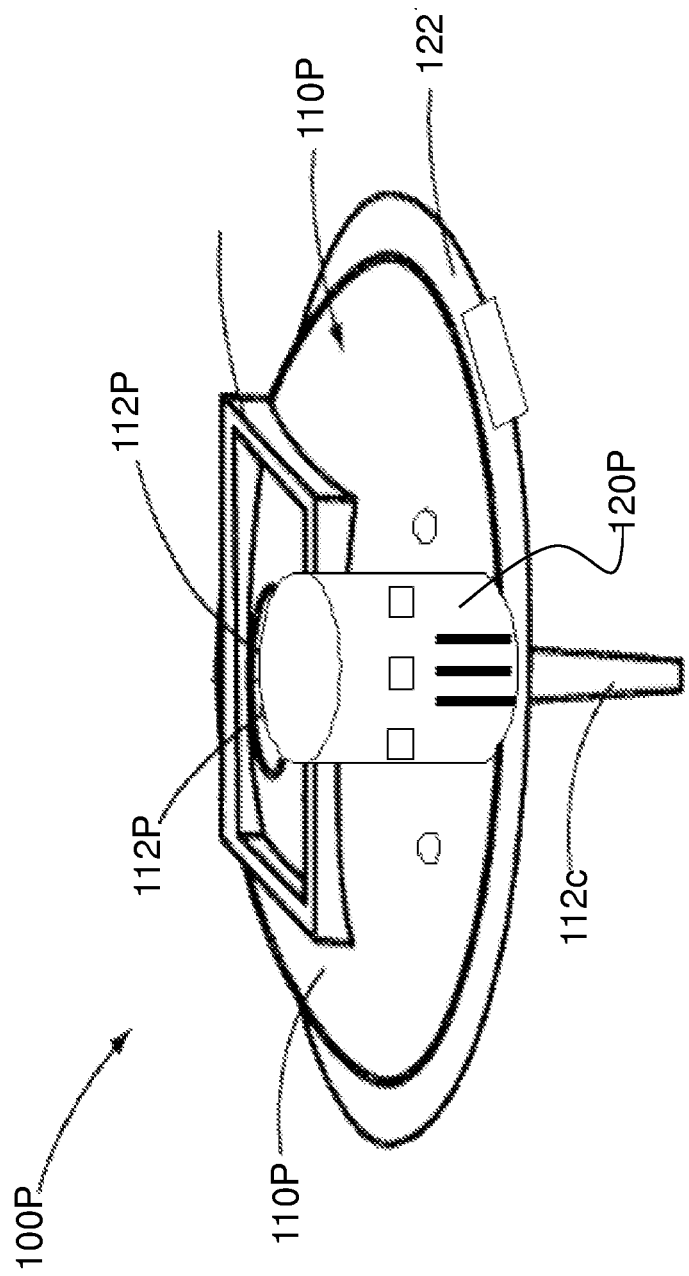
FIG. 8 is a schematic diagram of an optional drug delivery port optimizing device according to an optional embodiment of the present invention.

Most preferably disposable unit 110 comprises an injection area 112 (FIG. 2-7), 112P (FIG. 8). Optionally injection area 112 (FIG. 2-7) may be realized as predefined area of skin surface onto which a user may administer a subcutaneous injection transcending skin surface for example with a syringe, injection pen or the like syringe based drug delivery tool. Optionally injection area 112P may be realized in the form of drug delivery port through which a user may administer a subcutaneous drug dose without repeatedly accessing/traversing the skin surface, instead, using a cannula 112c (described in FIG. 8) to gain access the subcutaneous tissue.

Optionally disposable unit 110 may comprise at least one or more heating element 122h and/or a treatment element 122.

Most preferably reusable unit 120 provides the electronics module 128 that facilitates optimizing the drug delivery profile of the administered drug, most preferably insulin, therefore minimizing episodes of post prandial hyperglycemic and hypoglycemic events.

Reusable unit 120 most preferably comprises electronics module 128 and sensor module 120S. Most preferably electronics module 128 provides for activation reusable unit 120 by providing a controller, memory, communication capabilities, and by energizing the sensor module 120S.

Most preferably, electronics module 128 comprises a power supply module 128P, a controller module 128C, a communication module 128T, contactless communication module 128R and a memory module 128M. Optionally, electronics module 128 may further comprise user interface module 128U, provided for interfacing with the user that may appeal to the user by vision, sound, feel or touch (visual, audible or touch) for example including but not limited to a LED array, display, vibration piezoelectric element, speaker, or the like.

Optionally and preferably, power supply module 128P provides for providing power, controlling power and energy distribution as is known and accepted in the art. Optionally power supply 128P comprises a rechargeable power source that may be recharged by induction or with direct electrical contacts coupling. Optionally, power supply 128P may comprise rechargeable batteries, for example lithium ion batteries as is known in the art.

Optionally and most preferably, controller module 128C provides for overall master control of reusable unit 120, and may be provided in the form of a microcontroller as is known in the art. Optionally and preferably controller module 128C may comprise at real time clock or clock most preferably for obtaining a date and time stamp. Optionally, controller module 128C may be realized as a master control module for device 100. Optionally, controller 128C may be provided with a plurality of optional application and/or software adapted for data analysis of the available data and abstracting an optimized drug delivery profile and/or protocol. For example, optimized drug delivery profile and/or protocol may comprise adjusting and/or recalibrating an injection site heating profile for controlled via heating actuator 122h, or recalibrating dosage calculation via an insulin dosage calculator control that may be communicated to a user via communication module 128T.

Optionally and most preferably, communication module 128T may be provided to facilitate communication with reusable unit 120 and a plurality of optional devices comprising a corresponding communication module, for example base station unit 130. Optionally, communication module 128T may provide for optional forms of communication for example including but not limited to wireless communication, wired communication, cellular communication or the like as is known and accepted in the art.

Optionally and most preferably, contactless and/or near field communication may be realized in reusable unit 120 with module 128R for example provided in the form of a transponder capable of communicating and exchanging data over short distances, with a plurality of devices having corresponding electronics/circuitry. For example, reusable unit 120 may comprise an RFID reader (not shown) within contactless communication module 128R that is adapted for interfacing and communicating with a syringe based drug delivery device, for example, a syringe or injection pen having a corresponding RFID tag (158a-e). Most preferably, contactless communication module 128R may obtain data relating to a syringe and its contents, for example, including but not limited to syringe data, dosage utilized, drug type, drug details, drug lot number, drug handling (exposure to heat) or any data that may be made available on the RFID tag and/or contactless electronic s/tag/chip associated with the syringe or injection pen, or the deliverable drug and/or medicament associated therewith.

Optionally and most preferably, a memory module 128M functions to store and data log all events associated with and/or communicated to and/or interfaced with reusable unit 120 and optionally events associated with device 100. Optionally, memory module 128M may be realized as a volatile memory, and/or non-volatile memory, or any combination thereof. Optionally, memory module 128M may be realized in the form of removable non-volatile memory, for example as with a flash memory medium or the like as is known and accepted in the art.

Most preferably, sensor module 120S comprises a plurality of sensors and/or actuators provided to sense a user's environment and/or systemic metabolic environment and in light of that environment optimize the user's drug delivery profile so as to improve the Pharmacokinetic and Pharmacodynamic profile of the administered drug.

Sensor module 120S most preferably includes at least one or more treatment element 122 most preferably including at least one or more heating element 122h provided to apply heat over injection area 112 following an injection and configured to optimize the drug delivery profile. Most preferably sensor module 120S further comprises a meal detection sensor 126 and/or a physical activity monitor 124. Sensor module may further comprise impedance sensor 127 provided for detecting drug delivery, and physiological sensor 123 provided for detecting local physiological status such as blood perfusion about injection site.

Impedance sensor may for example be disposed about both the reusable unit 120 and disposable unit 110 and may include means for detecting a volume of the injected subcutaneous drug stored in a depot and adjusting the tissue treatment (e.g., an amount of the drug being injected) according to that measurement. Optionally, impedance sensor may be achieved, for example, by adding an electrode to disposable unit 110 that may be used for electrical impedance measurement where the reusable unit 120 comprises electronics 128 and a controller 128C to support the impedance measurement. Once the drug is infused to the subcutaneous tissue, it alters the impedance measurement result and as it clears from the depot the impedance measurement returns to the baseline. Thus, by tracking the impedance measurement, the device can detect the clearance of the drug from the subcutaneous depot and the treatment of the tissue may be adjusted accordingly. For example, the treatment element 122 may be controlled based on the volume of the drug depot as well as on the velocity by which the drug clears from the depot, provided with impedance sensor 127, so that when the depot is cleared the treatment, for example heating, stops or if the clearance velocity is low, the treatment, for example heat, may be increased.

Optionally and preferably, control of treatment element 122 and in particular heating element 122h is provided to optimize drug delivery and most preferably optimize in lieu of a plurality of data available to reusable unit 120, for example, including but not limited to intrinsic data available from sensor module 120S and external data communicated to unit 120, for example, with communication module 120T and/or contactless communication module 120R. Optionally intrinsic data may for example include but is not limited to a meal state obtained with meal sensor 126, local blood perfusion at injection site provided with physiological sensor 123, systemic physiological data provided with activity sensor 124 or the like. Optionally, external data available to unit 120 may for example include but is not limited to intended drug dose provided with module 128T, actual drug dose delivered provided with module 128R, type of drug delivered provided with module 128R, caloric analysis of meal consumed provided with module 128T.

Most preferably, activity monitoring sensor 124 provides for automatically and/or autonomously identifying activity of a user, for example, including registering caloric burn rate, walking events, exercise events, sleep events, steps or the like event. Most preferably the data made available by activity monitoring sensor 124 facilitates mapping user's activity relative to injection events and optionally meal events therein providing for optimizing and fine control of the systemic metabolic process of glucose and insulin, in attempting to minimize therefore minimizing episodes of post prandial hyperglycemic and hypoglycemic events, as previously described. For example, an insulin injection immediately following exercise and a meal has great implications for the control and optimization of insulin's systemic metabolic process especially when compared to an injection event following a meal event without any exercise. In such situation the approach to optimize insulin, for example by way of heating the injection site 112 following injection, so as to avoid post prandial hyperglycemic and hypoglycemic events are vastly different. For example, the heating profile and control parameters utilized for the optimization process following the injection may similarly be vastly different with new available data. Optionally, physical activity sensor 124 may for example be realized with at least one or more of pedometer, altimeter, gyro-sensor, accelerometer, the like or any combination thereof.

Most preferably, meal detection sensor 126 may be realized in the form of at least one or more microphones provided to detect a meal event. Optionally, meal sensor 126 may detect a meal event by recognizing sounds associated with a meal event. Optionally, meal sensor 126 may require device 100 to be placed in and around the abdominal section so as to ensure that a meal event is automatically detected based on sound emanating from the GI tract over the abdominal section of the user.

Most preferably, base station 130 provides for charging and powering reusable unit 120. Most preferably, base station 130 is powered with a main power supply. Optionally and preferably, base station 130 comprises electronics for example including but not limited to communication module 138, memory module 136, power supply module 134 and controller module 132. Optionally, data exchange between reusable unit 120 and charger 130 may be provided with communication module 138.

Optionally, memory module 136 may be utilized to exchange and communicate data between reusable unit 120 and memory module 128M. Optionally, memory 128M may be utilized as short term memory while, reusable portion is in use, and memory module 136 provides long term memory, storing data over time.

Optionally, controller 132 may be provided with and run a plurality of optional applications and/or software adapted for data analysis of the available data and abstracting an optimized drug delivery profile and/or protocol. Optionally, controller module 132 may comprise at real time clock or clock most preferably for obtaining a date and time stamp. For example, optimized drug delivery profile and/or protocol may comprise adjusting and/or recalibrating an injection site heating profile for control via treatment element 122, or recalibrating dosage calculation via an insulin dosage calculator control that may be communicated to at least one or reusable unit 120 and/or a user via communication module 128T.

Now referring to FIGS. 2-5, showing an optional embodiment of syringe based drug delivery optimizing device 100. FIG. 2A shows functional unit 102 comprising an optional disposable unit 110 coupled with an optional reusable unit 120. Reusable unit 120 is associated with disposable unit 110 by associating in a snap in manner where unit 120 snaps into disposable unit 110 within frame 110f between corresponding snap in recess 110r and 120r. Unit 120 further couples with a plurality of press fit coupling members 110c.

FIG. 2A shows device 100 in the functional closed configuration where disposable unit 110 is coupled over an injection area 112 with biocompatible adhesive 110a, where to gain access to the syringe based injection area 112 the device has to assume the open configuration as shown in FIG. 2B.

FIG. 2B depicts device 100 in the open, "ready for injection" configuration exposing injection area 112 and awaiting user's syringe based injection therein. FIG. 2B shows the single use injection area 112 as an open recess and/or window within disposable unit 110. Most preferably injection area 112 provides for a single use period of about 24 hrs, and further shows heating sensor and actuator 122h shaped to fit over the injection area. Optionally injection area 112 may be about 2 cm by 4 cm.

FIG. 3A shows an optional embodiment of a disposable unit 110 comprising an adhesive surface 110a that is most preferably covered by a laminate. Unit 110 includes a lower surface 110L and upper surface 110U that are coupled over a hinge 116 and may be functionally opened or closed relative to one another in claim shell manner. Most preferably upper surface 110U comprises a recess 110r, and press fit members 110c for facilitated secure coupling of the disposable unit 120 with reusable unit 110. Most preferably unit 110 comprises an activation member/pin 118 that most preferably automatically activates unit 120 when engaged with a corresponding recess 128a while the optimizer 100 is closed, and deactivates unit 120 when pin 118 is disengaged with recess 128a. Most preferably upper unit 110U provides for associating with unit 120 while lower surface 110L provides a surface for associating with a user skin surface utilizing adhesive layer 110a.

FIG. 4A provides a perspective view of reusable unit 120 showing indicator 120i, for example provided in the form of a LED indicator light.

Heating actuator 122h is shown about the lower surface of reusable unit 120. Most preferably heating actuator 122h or the like treatment elements 122 may be sized in accordance with and corresponds with injection site 112.

FIG. 4B provides a cross-section view of unit 120 revealing electronics module 128, heating actuator 122h, and heat sensor/thermister 122t providing for optimizing drug delivery about injection site 112 as previously described. FIG. 4B further depicts activating member 128a shown in the form of a recess associated with an activation switch that activates/deactivates electronics module 128, when engaged with activating pin 118 disposed about disposable member 110. Most preferably engagement of pin 118 with recess 128a provides an indication to controller module 128C of the status of device 100 that is indicative of open or closed configuration.

Unit 120 is most preferably provided in a housing 120h adapted for securely associating with and/or coupling with disposable unit 110 via at least one or more coupling. Optionally and preferably housing 120h is provide with a recess 120r that corresponds with a recess the disposable unit upper surfer 110U therein facilitating coupling between units 110 and 120.

FIG. 5A shows a perspective view of base station 130 comprising a recess 130r for receiving and securely fitting with reusable unit 120 about its lower surface. Optionally and most preferably base station 130 provides for powering and/or recharging reusable unit 120. Optionally and preferably base station recharges reusable unit 120 through at least two contacts 130c, having corresponding contacts about reusable unit 120. Optionally base station 130 may provide for recharging unit 120 by induction.

Most preferably base station unit 130 is powered with a main power supply via power cord 130p.

FIG. 5B depicts unit 120 docketed with base station 130, during recharging. Optionally recharging status of unit 120 may be displayed via indicator 120L Optionally while docketed unit 120 may communicate with station 130 to perform a data exchange dump. Optionally data exchange between unit 120 and 130 may be provided via contactless communication for example including but not limited to RFID, optical, near field communication, wireless, cellular or the like. Optionally while unit 120 is docketed within base station 130 data exchange may be provided for wired communication to delivery data collected during use of unit 120.

FIG. 6A-D shows an optional configuration for device 100 shown as a hinged optimizer 101 comprising hinged disposable unit 111 and hinged reusable unit 121. The operation and function of the device 101, disposable unit 111, reusable unit 121 are the same as those described earlier in FIGS. 1-5. Hinged optimizer 101 is characterized in that it comprises a two member hinge connector provided for coupling disposable unit 111 and reusable unit 121. Most preferably a first hinge member is disposed about unit 111 and a second disposed about 121. Optionally and preferably unit 111 comprises a male hinge connector 110h as shown, and reusable unit 121 comprises a corresponding female hinge connector 121h, provided for forming hinge 116h. Optionally disposable unit 111 may comprise a female hinge connector while reusable unit 121 may comprise a male hinge connector.

Optionally and most preferably hinge 116h provides a connector comprises single use period protection such that when hinge 116h is disassembled it renders disposable portion non-functional. Most preferably single use period protection of optimizer 101 provides for ensuring that an injection site 112 is used for the prescribed single use period, for example a period of about 24 hours with device 101. Single use period protection means with optimizer 101 are most preferably provided about hinge 116h with ensuring that a user couple or decouple disposable unit 111 and reusable unit 121 must occur at a reflex angle such that hinge 116h and cannot be coupled/decoupled while attached over an injection site over a user's skin surfaces without rendering unit 111 essentially non-functional. Once removed from the injection site disposable unit 111 is optionally and most preferably renders adhesive surface 110a non-functional.

Another alternative to realize single use period protection is by using electronics on the reusable unit 121 in conjunction with electronic recognizable and modified elements on the disposable unit 111, such that the number of times the disposable unit may be used is reduced with any additional use of any of reusable units 121 with a specific disposable unit 111.

FIG. 6A shows a perspective view of disposable unit 111 comprising one surface having an adhesive surface 110a covered with a laminate as shown, and an injection site window and/or recess 112. Disposable unit 111 further comprises activation pin 118, as previously described, as well as coupler 110c provided in the form of a press-fit latch coupler ensuring fastening of unit 121 with unit 111 when closed.

FIG. 6B shows a perspective view of reusable unit 121 showing female hinge members 121h, that most preferably provides for coupling at a reflex angle for example 270 degrees as a single time period measure as previously described.

FIG. 6C shows hinged optimizer 101 in its closed configuration where coupler 110c fits with unit 121 opposite the hinge member 116h.

FIG. 6D shows hinged optimizer 101 in its open configuration further showing activation pin 118 and coupler 110c. Activation pin 118 functions as previously described and provides an indication of the open or closed state of optimizer 101, while automatically activating an appropriate heating protocol once pin 118 engages with recess 128, as previously described.

Now referring to FIGS. 7A-C showing an optional embodiment of the present invention, device 105 comprising disposable unit 115, reusable unit 125 and base station 135. Most preferably disposable unit 115 comprises an injection site recess window 112, a biocompatible adhesive with laminate as previously described, and an integrated heating element (not shown). Most preferably disposable unit heating elements are energized by reusable unit 125 over electrical contacts 125c, shown in FIG. 7B. Accordingly, unit 125 comprises all functionality of the previously described 120 with the exception of an internal heating element provided for by disposable unit.

Most preferably base station 135 functions in the same manner as base station 130 previously described.

Now referring to FIG. 8 showing an optional embodiment of the present invention that, wherein device 100 is adapted for drug delivery realized as a drug delivery port 100P. Device 100P most preferably comprises a disposable port member HOP and reusable port member 120P.

Most preferably disposable port member 110P comprises a port injection area 112 that leads to a cannula 112c. Optionally heating actuator and/or member 122h or optional treatment element 122 may be disposed on either of disposable unit 110P and/or on reusable unit 120P.

Optionally and preferably at least one and/or both of reusable unit 120P and disposable unit HOP may be configured to have single use period of up to about three days. Optionally, unit 120P may be provided with sufficient battery power to last the length of the single use period. Optionally disposable unit HOP may be provided with an adhesive layer that is rendered non functional after the length of the single use period for example three days.

Figure 9A:
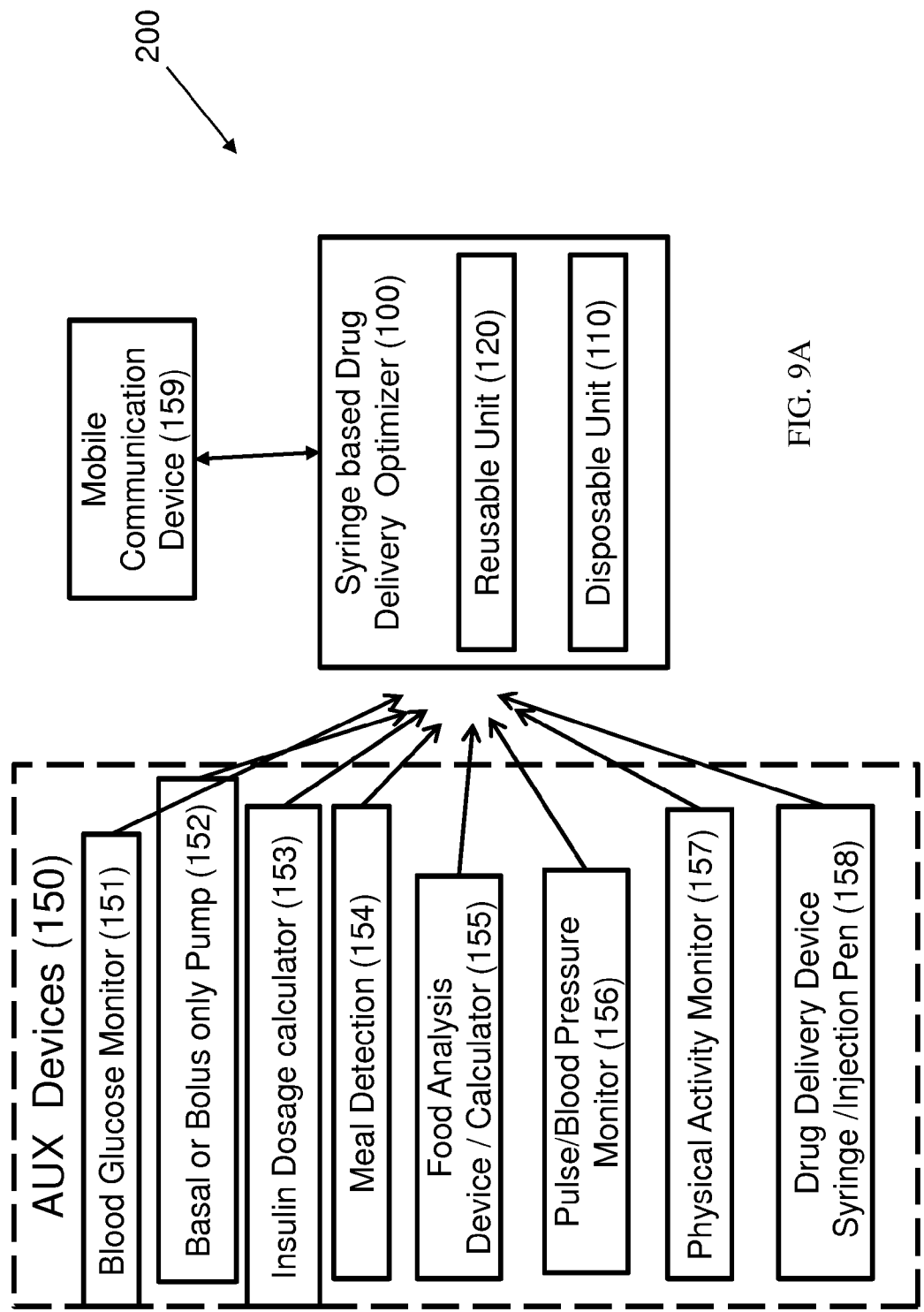
FIG. 9A is a schematic block diagram of a system according to an optional embodiment of the present invention including a drug delivery optimizing device, a mobile communication device and optional auxiliary devices according to the present invention.

Now referring to FIG. 9A showing a schematic block diagram of an optional system 200 according to the present invention, system 200 is centered about optimizer 100, 100p, 101 as previously described where most preferably data exchange and controlling functionally is facilitated with the controller 128C, 132 and communication module 138, 128T of either or both reusable unit 120 and/or base station 130, as previously described.

Optionally and most preferably system 200 provides for interfacing the optional optimizers 100 according to optional embodiments of the present invention 100, 101, 100p, 105 with a plurality of optional auxiliary devices 150, in order to provide optimizing the systemic metabolic process and control blood glucose and insulin levels with syringe based drug delivery devices for example including but not limited to a syringe or injection pens. System 200 most preferably provides for optimizing drug delivery by optimizing the drug delivery profile of the administered drug, most preferably insulin, therefore minimizing episodes of post prandial hyperglycemic and hypoglycemic events. Most preferably system 200 provides for this by monitoring and correlating of data types all relating to the drug delivery profile of insulin so as to be as proactive as possible with respect to controlling and balancing glucose and insulin levels.

As previously described, optimizer 100 provides for optimizing drug delivery by controllably applying heat over an injection area following syringe based drug administration, while controlling the heating cycles and parameters based on a wide spectrum of user related data that affects the systemic metabolic process related the administered drug, for example insulin. Most preferably device 100 provides for proactive controlling of insulin metabolic by way of syringe based drug delivery therein optimizing and therefore minimizing episodes of post prandial hyperglycemic and hypoglycemic events.

Most preferably device 100 optimizes insulin absorption by comprising at least one and more preferably two or more sensors and actuators configured to automatically and seamlessly provide data relating to user's meal status, meal timing, the timing of administered drug, drug dose, drug type, logging user activity, analyzing user physical activity, controlled heating of the injection area, any combination thereof or the like.

System 200 provides for associating and or providing device 100 with further data available from a plurality of optional auxiliary device 150 for example including but not limited to Blood Glucose Monitor 151, Basal or Bolus only Pump 152, Insulin Dosage calculator 153, Meal Detection device 154, Food Analysis Device/Calculator 155, Pulse/Blood Pressure Monitor 156, Physical Activity Monitor 157 and Syringe based Drug Delivery Device Syringe/Injection Pen 158, or the like as is known in the art. Most preferably some auxiliary devices provide first hand data relating to the systemic metabolic process, for example, blood glucose monitor 151 most preferably measure blood glucose levels and communicates the data to device 100, that most preferably may then be stored in at least one or both of reusable unit memory module 128M and/or base station memory module 136.

Optionally Basal or Bolus only Pump 152 may provide device 100 with data relating to a users administration of basal insulin.

Optionally Insulin Dosage calculator 153 may provide device 100 with data relating to a user's insulin dosage, where such data may be utilized by device 100 to further optimize drug delivery dose and/or heater profile via controller module 128C, 132 in the reusable unit 120 or base station 130.

Optionally and auxiliary meal detection device 154 may provide device 100 with further data relating to a user's external meal state beyond the data intrinsically available through Sensor module 120S as previously described.

Optionally Food Analysis Device/Calculator 155 may provide device 100 with data relating to an analysis of the food consumption and caloric intake and/or count that may have directly affected the drug delivery profile utilized by device 100.

Optionally Pulse/Blood Pressure Monitor 156 may provide device 100 with data relating to the cardiovascular system that may have indirect affect on insulin's drug delivery profile.

Optionally Physical Activity Monitor 157 may provide device 100 with further data relating to a user's external physical activity beyond the data intrinsically available through sensor module 120S as previously described.

Most preferably Syringe/Injection Pen 158 provide device 100 with further data relating to a user's use of a syringe and/or injection pen both for bolus and basal injection for example including but not limited to dosage utilized, drug type, drug details as previously described optionally and preferably through at least one or more associated contactless communication device 158a-e, for example an RFID tag or passive tag, for example as shown in FIG. 9B. Most preferably as syringe based drug delivery device 158 nears an optional optimizer 100, 101, 105, 100P data relating to both the delivery pen and its contents for example drug, medicament, insulin, may be communicated from syringe drug delivery device 158 to reusable unit 120 of optimizer 100 via contactless interaction between at least one or more syringe based drug delivery device tags 158a-e, and contactless communication module 128R allowing optimizer 100 to register all available date both relating to device and associated drug with device 158 to store and correlate that information to optimizer 100.

Optionally the data passed from drug delivery device 158 may for example include but is not limited to, drug delivery device identification, injection date and time stamp, dose delivered, drug identification, drug lot number, drug manufacturing details, delivered dose, type of drug, environmental exposure associated with the drug, type of delivery device used, time stamp of delivery, injection time length, location of injection or the like. Data related to the syringe 158 and its contents available on tags 158a-e provide for optimizing drug delivery to a user as well as providing detailed information to a user and/or optimizer 100 that may be identified as potentially problematic and/or hazardous to a user.

Figure 10:
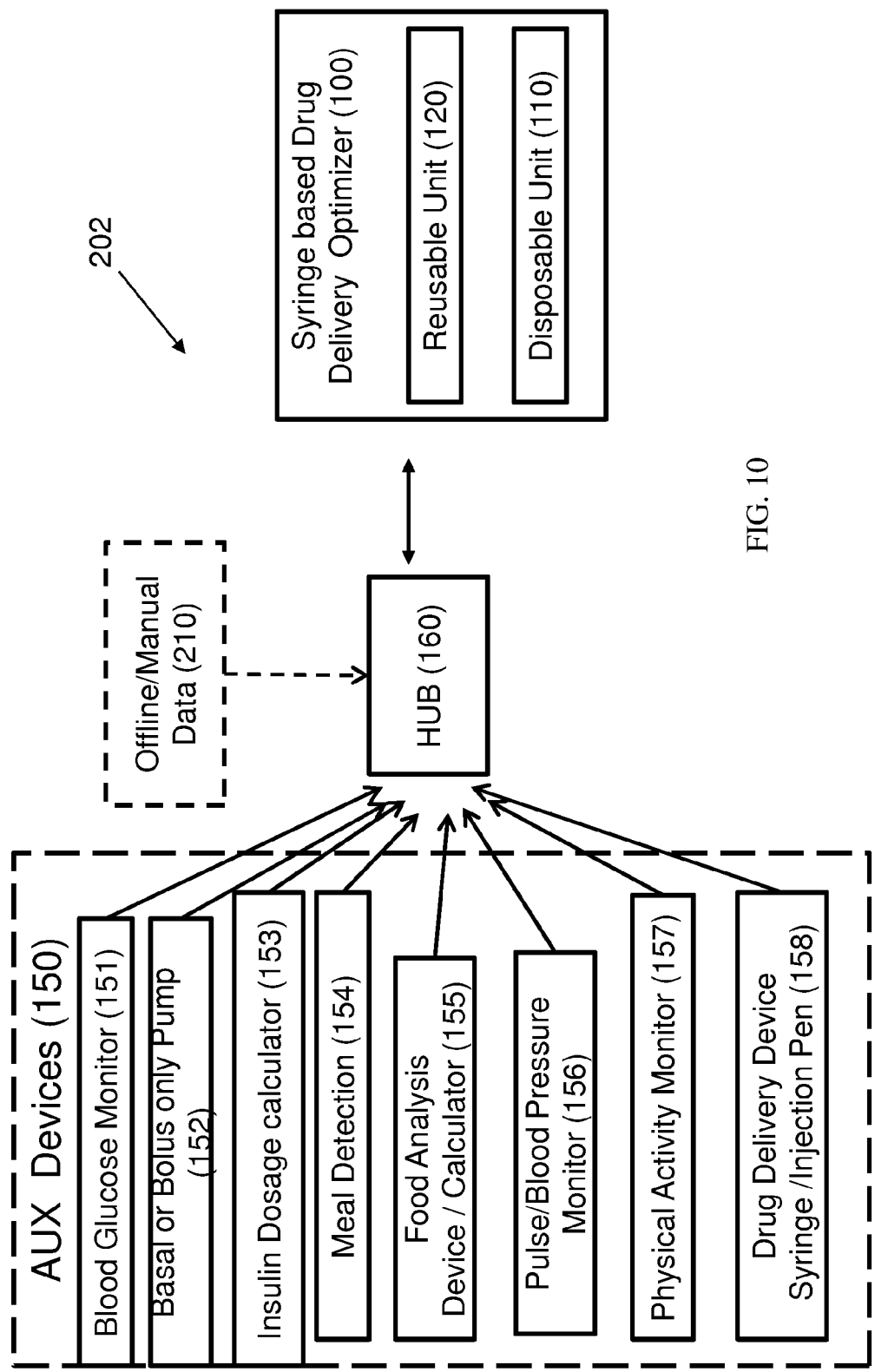
FIG. 10 is a schematic block diagram of a system according to an optional embodiment of the present invention including a drug delivery optimizing device and a HUB with optional auxiliary devices according to the present invention.

For example, a user may confuse one injection type for another where instead of injection of basal insulin the user injects is about to inject bolus insulin, optimizer 100 most preferably may identify such situations and communicate to an optional user interface 128U (FIG. 1) or communicate the information to a user via mobile communication device 159 (FIG. 9A) or HUB 160 (FIG. 10).

Optionally communication between auxiliary device 150 and device 100 may be facilitated with and or through mobile communication device 159. Optionally mobile communication device may be provided in optional forms for example including but not limited to PDA, laptop, smart phone, tablet or the like mobile communication device comprising a processing and communication capabilities. For example, a food analysis calculator 155 may be provided in the form of a software application running on mobile communication device 159 that communicates data relating to caloric calculation to device 100 to at least one of base station 130 or reusable unit 120.

Optionally mobile communication device 159 may facilitate communication and entry of optional offline data 210 to device 100 to at least one of base station 130 or reusable unit 120. For example, offline data 210 may for example include but is not limited to laboratory tests, a user's medical history or the like data that may play a role in the systemic insulin metabolic pathway affecting the homeostasis between glucose levels and insulin levels.

FIG. 10 depicts a schematic block diagram of an optional system 202 according to the present invention where communication between at least one or more auxiliary devices 150 and optimizers 100, 105, 101, 100P is facilitated and controlled through a dedicated processing HUB 160 that may for example be realized in the form of a mobile communication device 159. Optionally and preferably HUB 160 may be utilized as the central controlling device of system 202 providing for memory, data processing and overall system management to determine a plurality of parameters relating to the optimization and control of syringe based drug delivery through device 100. Most preferably system 202 provides a system that integrates a plurality of data types that provides for learning and updating individualized/personalized drug delivery metabolic pathway related to a syringe based drug delivery device. Most preferably processer disposed in HUB 160 provides for integrating further offline data 210 for example including but not limited to medical history or the like patient specific data.

Figure 11:
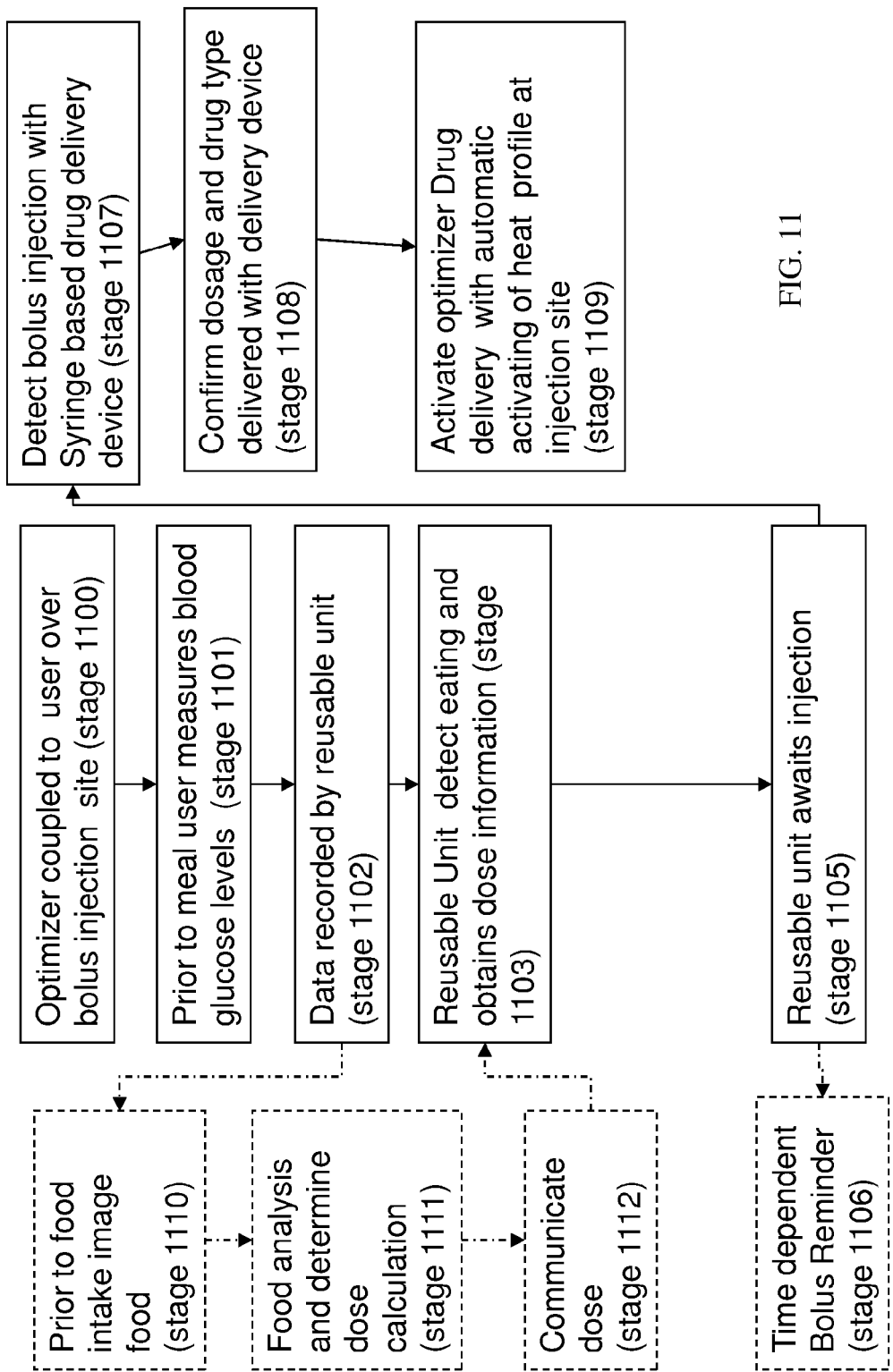
FIG. 11 is a flow chart of an exemplary method according to the present invention.

FIG. 11 shows a flowchart of an optional embodiment of the present invention for optimizing drug delivery profile with the optimizer 100, 101, 105, 100P, according to optional embodiments of the present invention.

First in stage 1100 a drug delivery optimizer 100, 101, 105, 100P is coupled to a user defining a bolus drug delivery injection site 112 over a user's skin surface. Next in stage 1101, prior to an expected meal time bolus injection user checks blood glucose levels with a blood glucose monitor 151. Optionally and preferably blood glucose monitor 151 is synchronized and in communication with reusable unit 120, for example, via communication module 128C. Next in stage 1102, reusable portion 120, stores the blood glucose reading from stage 1101.

Optionally and more preferably in parallel to meal event the user prior to food intake the user utilizes a food analyzing device and/or calculator 155 and dose calculator 153 to determine both the caloric value of the meal and the required insulin does based on the expected meal content and caloric value, as shown in optional stages 1110 and 1111. Finally in optional stage 1112 the calculated dose is communicated to unit 120. Most preferably when expected dose is communicated to device 100, 101, 105, 100P its reusable unit 120 can store the information of what dose and insulin type to expect in the bolus injection. Furthermore, device 100 most preferably may utilize the data to determine the optimization scheme required, to most effectively drug delivery by way of controlling the appropriate treatment element 122, for example including heating element 122*h*.

Next in stage 1103, reusable unit 120 detects meal event most preferably via sensor module 120S and in particular through meal detection sensor 126. Optionally meal detection may be further provided by way of communication with an auxiliary meal detection device 154. Most preferably once meal event is detected, reusable unit 120 records the meal event with a time stamp. Optionally and preferably in stage 1103 unit 120 further obtains expected insulin dose based on the detected meal and/or blood glucose levels measured in stage 1102.

Next in stage 1104 once meal has been detected unit 120 awaits detection of a bolus injection. Most preferably bolus injection is most preferably detected by the change in configuration of unit 120 for example with activation pin 118 providing for detecting closed or open configuration of optimizer 100 where reusable unit 120 is opened relative to disposable unit 110. For example, in preparation for a bolus injection, unit 120 is opened therein activation pin 118 is disengaged from recess 128*a*, following injection unit 120 is closed onto disposable unit 110 therein reengaging activation pin 118 and recess 128*a* indicating that optimization may begin and/or continue about the injection site 112.

Accordingly in stage 1105 optimizer 100 awaits for bolus injection, if such a bolus injection is not detected within a given time frame an optional reminder may be provided, in stage 1106.

Next in stage 1107, optimizer 100 detects a bolus injection with a syringe based drug delivery device. Most preferably syringe based drug delivery is detected with contactless communication between module 128R and a syringe or injection pen 158 comprising corresponding electronics, for example a RFID tag, as previously described, shown in FIG. 9B. Most preferably administration of drug dose with syringe based drug delivery device 158 near and/or within range of unit 120 and particularly contactless communication module 128R, causes disposable unit 120 to record the injection event along with all available data associated with the syringe based delivery device 158 that may be made available via at least one or more contactless communication electronics and/or tags 158*a-e*. Optionally the data available on tag 158*a-e* may, for example, include but is not limited to delivered dose, type of drug, drug lot number, environmental exposure associated with the drug, type of delivery device used, time stamp of delivery, injection time length, location of injection or the like. Most preferably injection events are stored in memory module 128M.

Next in stage 1108 the data associated with the injection communicated in stage 1107 is confirmed to ensure that the proper drug type and dose was actually delivered to the user. Optionally and most preferably if any problems are identified due to mismatch of dose and/or drug type relevant communication is initiated from unit 120 most preferably through communication module 128T, optionally to a HUB 160 or mobile communication device 159.

Next in stage 1109 following injection optimizer 100 optimizes drug delivery by activating, as necessary, treatment element 122 for example heating element 122*h* about the injection site 112. Optionally and preferably optimization is controlled relative to the data available to optimizer 100 for example with intrinsic sensor including physical activity sensor 124 and/or physiological sensor 123 for example indicative of local blood perfusion, impedance level with impedance sensor 127; and further optimized relative to external data communicated to optimizer 100, either directly (FIG. 9A) or indirectly via HUB 160 (FIG. 10), from at least one or more auxiliary device 150, as previously described.

Figure 12:
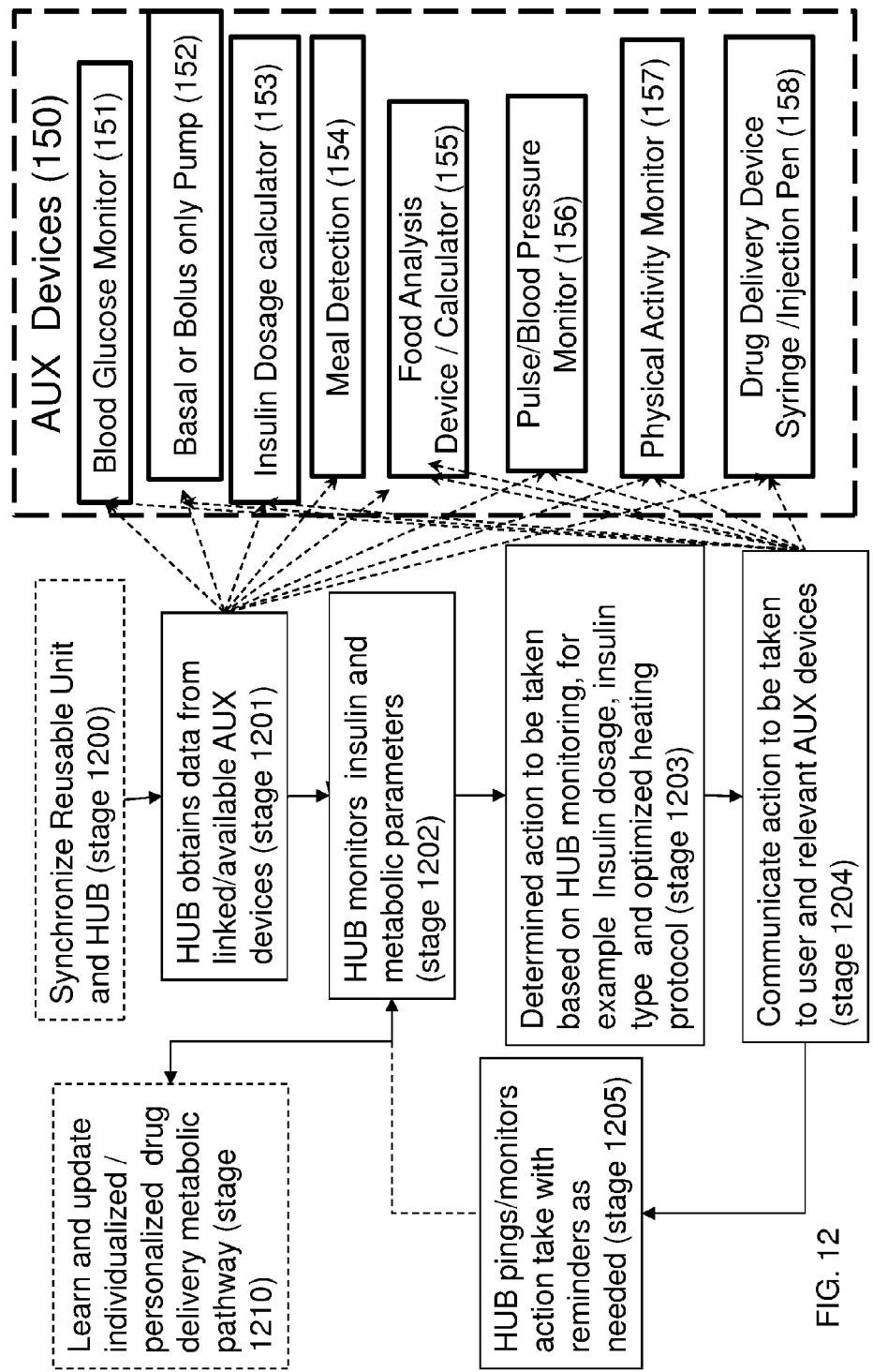
FIG. 12 is a flow chart of an exemplary method according to the present invention.

FIG. 12 provides a flow chart of an optional method according to the present invention, utilizing system 202 described in FIG. 10, where a HUB 160 provides a central processing and integration unit to facilitate the information gathered by optimizer 100 according to the present invention, therein providing individualized and/or personalized drug delivery profile for individuals using a syringe based drug delivery devices 158 such as a syringe and or injection pen to control at least one or both of basal and bolus insulin injection to ensure individualized homeostatic blood glucose levels and avoidance, limit or minimize of hyperglycemic and hypoglycemic events.

First in stage 1200 communication is synchronized between HUB 160 and device 100, 101, 105, 100P most preferably about reusable unit 120 and optionally about base station 130.

Next in stage 1201 HUB 160 data from all available and linked AUX devices 150 as previously described.

Next in stage 1202 HUB 160 monitors and integrates all data sources that relate to insulin metabolic processes.

Optionally based on this data, in stage 1210, HUB 160 abstracts and learns and continuously updates a personalized drug delivery profile and/or user specific metabolic pathway associated with the drug. Optionally stage 1210 may be realized with dedicated learning algorithms, neural networks, fuzzy networks or the like artificial intelligence tools as known and accepted in the art.

Next in stage 1203, based on data available to HUB 160 and local monitoring data provided by optimizer 100, determine any action to be taken to ensure continuous homeostatic levels of blood glucose levels, by a user or device linked and associated with HUB 160 for example including but not limited to auxiliary device 150 and optimizer 100.

Next in stage 1204 the required action is communicated to the appropriated linked device optimizer 100 and/or at least one or more auxiliary device 150.

Next in stage 1205, HUB 160 monitors action communicated in stage 1204 is performed or optionally alternates the action to be taken should a required action is not performed at all or in a timely manner.

There are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Importantly, the Summary may not be reflective of or correlate to the inventions protected by the claims in this or continuation/divisional applications hereof. Even where this Summary is reflective of or correlates to the inventions protected by the claims hereof, this Summary may not be exhaustive of the scope of the present inventions.

While the invention has been described with respect to a limited number of embodiment, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

Further modifications of the invention will also occur to persons skilled in the art and all such are deemed to fall within the spirit and scope of the invention as defined by the appended claims.

While the invention has been described with respect to a limited number of embodiments, it will be appreciated that many variations, modifications and other applications of the invention may be made.

What is claimed is:

1. A device for facilitating drug delivery with a syringe based device, wherein the device optimizes the delivery of an injected drug, records activity and data relative to said drug injections while the drug is administered, the device comprising:
   a disposable unit configured for a single use period characterized in that said disposable unit is rendered non-functional after said single use period, the disposable unit comprising a lower surface having a biocompatible adhesive with removable laminate for coupling said disposable unit over an area of skin defining an injection area; and
   a reusable unit having electronics comprising: control module, memory module, power supply module, communication module, contactless communication module, treatment element module and sensor module,
   the disposable unit having at least one connector for coupling with said reusable unit and an activating member configured to activate said reusable unit,
   wherein said power supply module comprises a rechargeable energy source that may be replenished with a base station unit for charging said power supply,
   wherein the disposable unit comprises two surfaces and a member connecting an end of one of the surfaces to an end of the other of the surfaces.

2. The device of claim 1 wherein said single use period is any of: a) days of use, b) from about one day or up to three days, c) number of injection administered in the injection area, and d) at least 4 injections.

3. The device of claim 1 wherein said disposable unit is configured for use as a drug delivery port having a single use cannula over said injection area and a single use period of about three days.

4. The device of claim 1 wherein said reusable unit and disposable unit are moved relative to one another to assume a plurality of configurations including an open configuration and a closed configuration.

5. The device of claim 1 wherein said base station unit is adapted for receiving and securely associating with said reusable unit; said base station comprising a power supply module provided for recharging or powering said reusable unit and a communication module provided for communicating and data exchange with said reusable unit; and wherein said base station unit charges said reusable unit via electrical contacts or by induction.

6. The device of claim 1 wherein said reusable unit communication module provides for communicating and interfacing with at least one or more auxiliary devices selected from the group consisting of: a mobile communication device, a meal detection device, a blood glucose monitor, a physical activity detector, a syringe, a syringe based device, a drug delivery pen, a caloric intake calculator, a food analysis device, a basal only pump, a bolus only pump, a blood pressure and a pulse monitor, and any combination thereof.

7. The device of claim 1 wherein said communication module may be selected from the group consisting of: contactless communication, near field communication, wireless communication, cellular communication, RFID based communication, Bluetooth, WiFi, ZigBee, optical communication, and piezoelectric/acoustic communication.

8. The device of claim 1 wherein said contactless communication module is adapted for interfacing with a syringe based drug delivery device fit with at least one or more corresponding contactless electronic identification circuitry for identifying and communicating data associated with the syringe based delivery device data and drug contents.

9. The device of claim 8 wherein data communicated from said syringe based drug delivery device is selected from the group consisting of: drug delivery device identification, injection date and time stamp, drug identification, drug lot number, drug manufacturing details, delivered dose, type of drug, environmental exposure associated with the drug, type of delivery device used, time stamp of delivery, injection time length, location of injection, and any combination thereof.

10. The device of claim 9 wherein data communicated from said at least one syringe based drug delivery device is utilized to optimize said drug delivery about said injection area.

11. The device of claim 1 wherein said sensor module comprises a meal detection sensor for detecting a user's meal state, and a physical activity sensor for detecting a user's physical activity and positioning or posture.

12. The device of claim 11 wherein said sensor module further comprises at least one or more sensors selected from the group consisting of an impedance sensor for identifying drug delivery status, physiological sensor for identifying the user's physiological parameters, and a treatment element for applying a treatment to a user before, after or during a syringe based drug administration.

13. The device of claim 12 wherein said treatment optimizes a drug delivery profile and improves the pharmacodynamic and pharmacokinetic drug profile.

14. A system for facilitating and managing drug delivery data from a plurality of syringe based drug delivery devices, the system including: the drug delivery optimizing device of claim 1 and at least one contactless electronic identification circuitry adapted for coupling or otherwise attaching to a syringe based drug delivery device for communicating injection data and administering drug data to said drug delivery optimizing device.

15. The system of claim 14 wherein said drug delivery optimizing device is interfaced and in communication with a mobile communication device or a HUB.

16. The system of claim 15 further comprising at least one auxiliary device selected from the group consisting of: a meal detection device, a blood glucose monitor, a physical activity detector, a syringe, a syringe based device, a drug delivery pen, a caloric intake calculator, a food analysis device, a basal only pump, a bolus only pump and a blood pressure monitor.

17. The system of claim 16 wherein the reusable unit of said drug delivery optimizing device provides for interfacing with said auxiliary devices, for integrating and storing data provided from individual said auxiliary devices.

18. The system of claim 17 wherein communication with said auxiliary devices is facilitated with said HUB or said mobile communication device.

19. A method for optimizing drug delivery with a syringe based drug delivery device with the system of claim 15, the method comprising:
associating said drug delivery optimizing device of claim 1 with said HUB;
associating a plurality of auxiliary devices with said HUB;
communicating data from said plurality of auxiliary devices and said syringe based drug delivery device to said HUB;
determining an optimization drug delivery protocol based on said communicated data that is abstracted relative to at least one goal for maintaining balanced blood glucose level; and
communicating the optimized drug delivery protocol to said drug delivery optimizing device.

20. A method for optimizing drug delivery with the drug delivery optimizing device of claim 11, the method comprising:
coupling said drug delivery optimizing device with a user for continuously recording user's daily activity with said physical activity sensor and a meal event with said meal detection sensor;
continuously communicating with at least one or more auxiliary devices for obtaining supplementary user data and storing said data;
during drug administration establishing contactless communication between said syringe based drug delivery device and said drug delivery optimizing device, both for bolus or basal drug delivery injections, to obtain syringe data including syringe identification, syringe parameters and data associated with the syringe contents, wherein data exchange is provided by said contactless communication module and wherein said communicated data is stored in said memory module of said drug delivery optimizing device, along with a date and time stamp; and
communicating all supplementary obtained data to said drug delivery optimizing device for controlling a treatment element provided to optimize drug delivery.

21. The method of claim 20 wherein said drug delivery optimizing device detects a mealtime event with said physical activity sensor and said meal detection sensor; and further comprises:
initiating a timer from detection of said meal time event and await a bolus injection;
providing a reminder as necessary;
detecting a pending injection through contactless communication with syringe based drug delivery device; and
initiating a drug delivery treatment protocol based on available data.

* * * * *